United States Patent [19]

Konishi et al.

[11] Patent Number: 4,708,872

[45] Date of Patent: Nov. 24, 1987

[54] ANTITUMOR ANTIBIOTIC COMPLEX

[75] Inventors: Masataka Konishi, Kawasaki; Kyoichiro Saitoh, Zushi; Hiroaki Ohkuma; Hiroshi Kawaguchi, both of Tokyo, all of Japan

[73] Assignee: Bristol-Meyers Company, New York, N.Y.

[21] Appl. No.: 812,699

[22] Filed: Dec. 23, 1985

Related U.S. Application Data

[63] Continuation of Ser. No. 768,764, Aug. 25, 1985, which is a continuation of Ser. No. 601,181, Apr. 20, 1984, which is a continuation-in-part of Ser. No. 495,231, May 16, 1983, abandoned.

[51] Int. Cl.$^4$ .......................... A61K 35/74; C12P 1/04
[52] U.S. Cl. ..................................... 424/115; 435/170
[58] Field of Search ................. 424/115, 117; 435/170

[56] References Cited

U.S. PATENT DOCUMENTS 4,530,835  7/1985  Bunge et al. ........................ 424/117

Primary Examiner—Jerome D. Goldberg
Attorney, Agent, or Firm—David M. Morse

[57] ABSTRACT

A novel antibiotic complex designated herein as BBM-1675 complex is produced by fermentation of certain novel strains of *Actinomadura verrucosospora*. The complex may be separated into two major components, BBM-1675 $A_1$ and $A_2$, and four minor components, BBM-1675 $A_3$, $A_4$, $B_1$ and $B_2$, and such components exhibit both antimicrobial activity and antitumor activity.

2 Claims, 14 Drawing Figures

NMR SPECTRUM OF BBM-1675 A1
(60 MHz IN CDCl$_3$)

NMR SPECTRUM OF BBM-1675 A2
(60 MHz IN CDCl$_3$)

NMR SPECTRUM OF BBM-1675 A3
(60 MHz IN CDCl$_3$)

NMR SPECTRUM OF BBM-1675-A4
(60 MHz IN CDCl₃)

INFRARED ABSORPTION SPECTRUM OF PURIFIED BBM-1675A1 IN KBr

PMR SPECTRUM OF PURIFIED BBM-1675 A1
(360 MHz IN CDCl₃)

13C NMR SPECTRUM OF PURIFIED BBM-1675 A1 (90.3 MHz IN CDCl3)

PMR SPECTRUM OF PURIFIED BBM-1675A2
(360 MHz IN CDCl₃)

13C NMR SPECTRUM OF PURIFIED BBM-1675 A2
(90.3 MHz IN CDCl3)

4,708,872

ANTITUMOR ANTIBIOTIC COMPLEX

CROSS-REFERENCE TO RELATED APPLICATION

This application is a continuation of our co-pending application Ser. No. 768,764 filed Aug. 25, 1985 which is a continuation of co-pending application Ser. No. 601,181 filed Apr. 20, 1984 which is a continuation-in-part of application Ser. No. 495,231 filed May 16, 1983, now abandoned.

BACKGROUND OF THE INVENTION

1. Field of the Invention

This invention relates to new antitumor antibiotic substances and to their production and recovery.

2. Description of the Prior Art

The antitumor antibiotic compounds of the present invention have not yet been identified in terms of structure. In view of their unique physical, chemical and biological properties, however, applicants believe that the BBM-1675 antibiotics are novel substances.

European Patent Publication No. 95154A1 discloses fermentation of *Actinomadura pulveraceus* sp. nov. No. 6049 (ATCC 39100) to produce antitumor antibiotics designated WS 6049-A and WS 6049-B. The structures of the WS 6049 antibiotics have not yet been elucidated, but the characterizing properties given for the antibiotics indicate that WS 6049-A and WS 6049-B may be related in structure to the BBM-1675 antibiotics of the present invention. Spectral data show, however, that neither WS 6049A nor WS 6049B is identical to any of applicants' BBM-1675 components. Moreover, the producing organism described in European Patent Application Publication No. 95154A1 may be clearly differentiated from *Actinomadura verrucosospora* employed in the present invention in the color of its aerial mycelium on ISP Medium Nos. 2, 3 and 4, in its positive milk peptonization and in its positive utilization of D-fructose, D-mannitol, trehalose and cellulose.

SUMMARY OF THE INVENTION

There is provided by the present invention a new antitumor antibiotic complex designated herein as BBM-1675, said complex being produced by cultivating a BBM-1675-producing strain of *Actinomadura verrucosospora*, most preferably *Actinomadura verrucosospora* strain H964-92 (ATCC 39334) or *Actinomadura verrucosospora* strain A1327Y (ATCC 39638), or a mutant thereof, in an aqueous nutrient medium containing assimilable sources of carbon and nitrogen under submerged aerobic conditions until a substantial amount of said BBM-1675 complex is produced by said organism in said culture medium, and optionally recovering the complex from the culture medium. Also provided by the present invention are two major bioactive components of BBM-1675 complex designated as BBM-1675$A_1$ and $A_2$ and four minor bioactive components of said complex designated BBM-1675$A_3$, $A_4$, $B_1$ and $B_2$. The components may be separated and purified by conventional chromatographic procedures. The BBM-1675 complex and its bioactive components exhibit both antimicrobial and antitumor activity.

DETAILED DESCRIPTION

Figure 1:
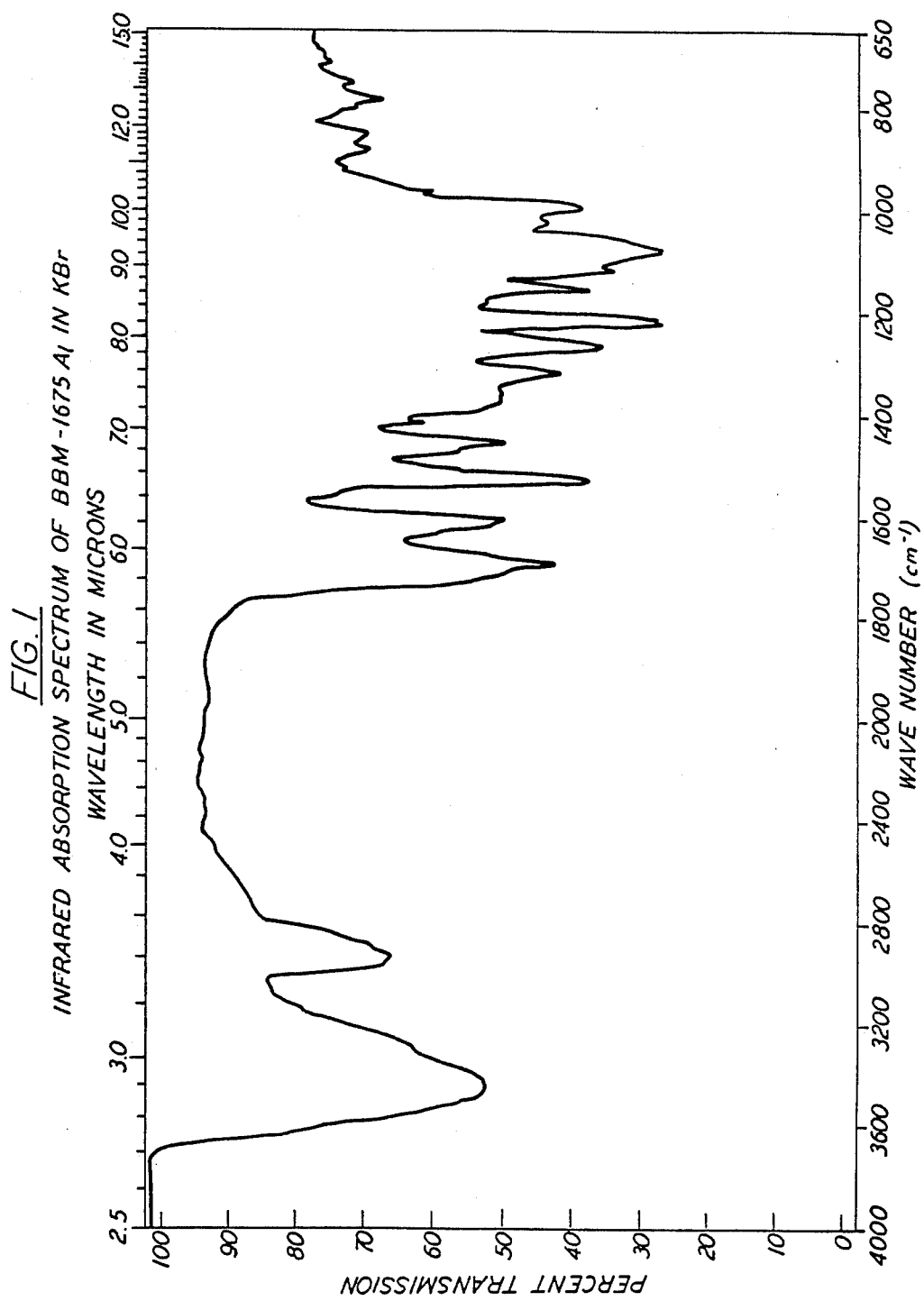
FIG. 1 shows the infrared absorption spectrum of partially purified BBM-1675 $A_1$ (KBr pellet).
Figure 2:
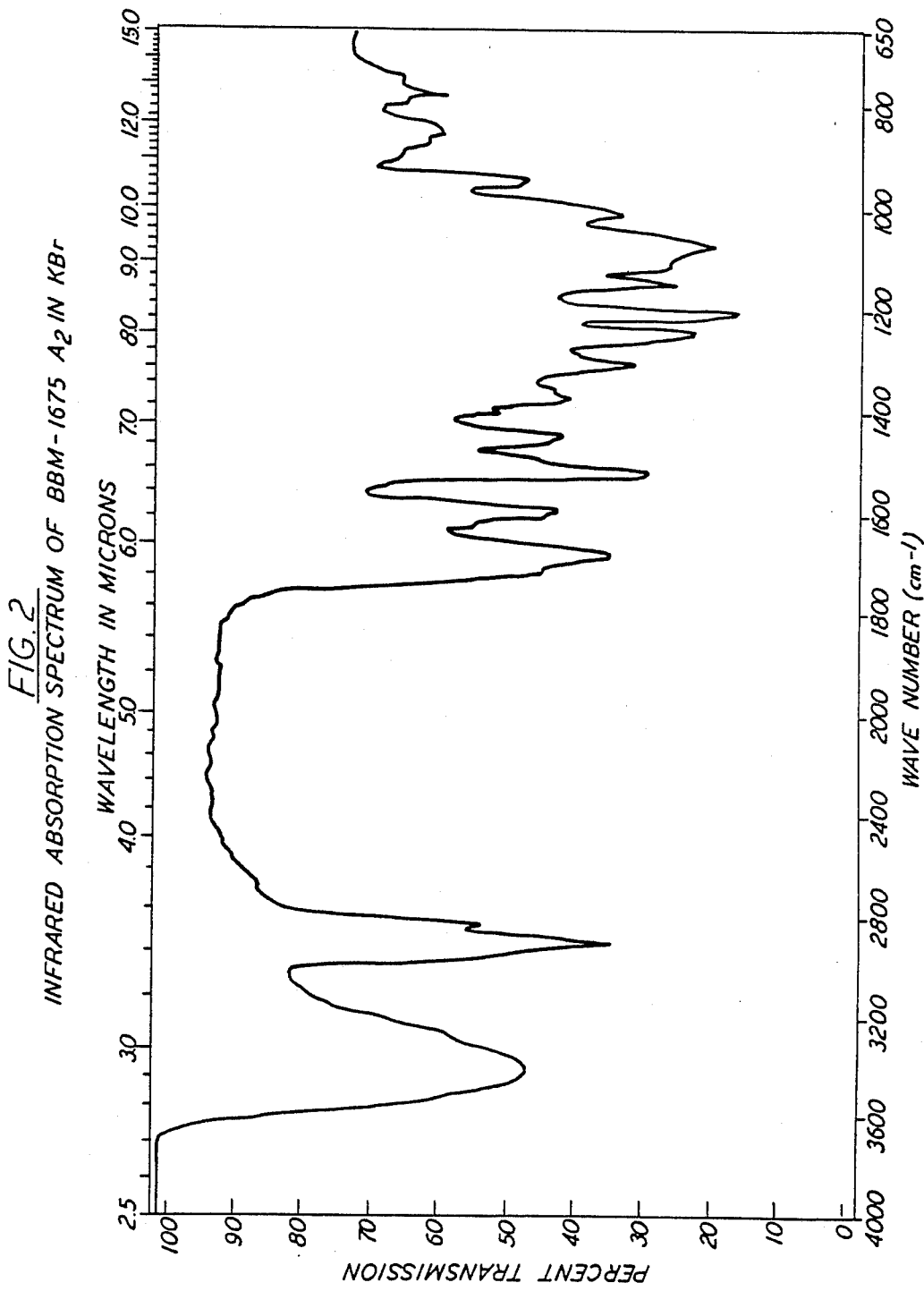
FIG. 2 shows the infrared absorption spectrum of partially purified BBM-1675 $A_2$ (KBr pellet).
Figure 3:
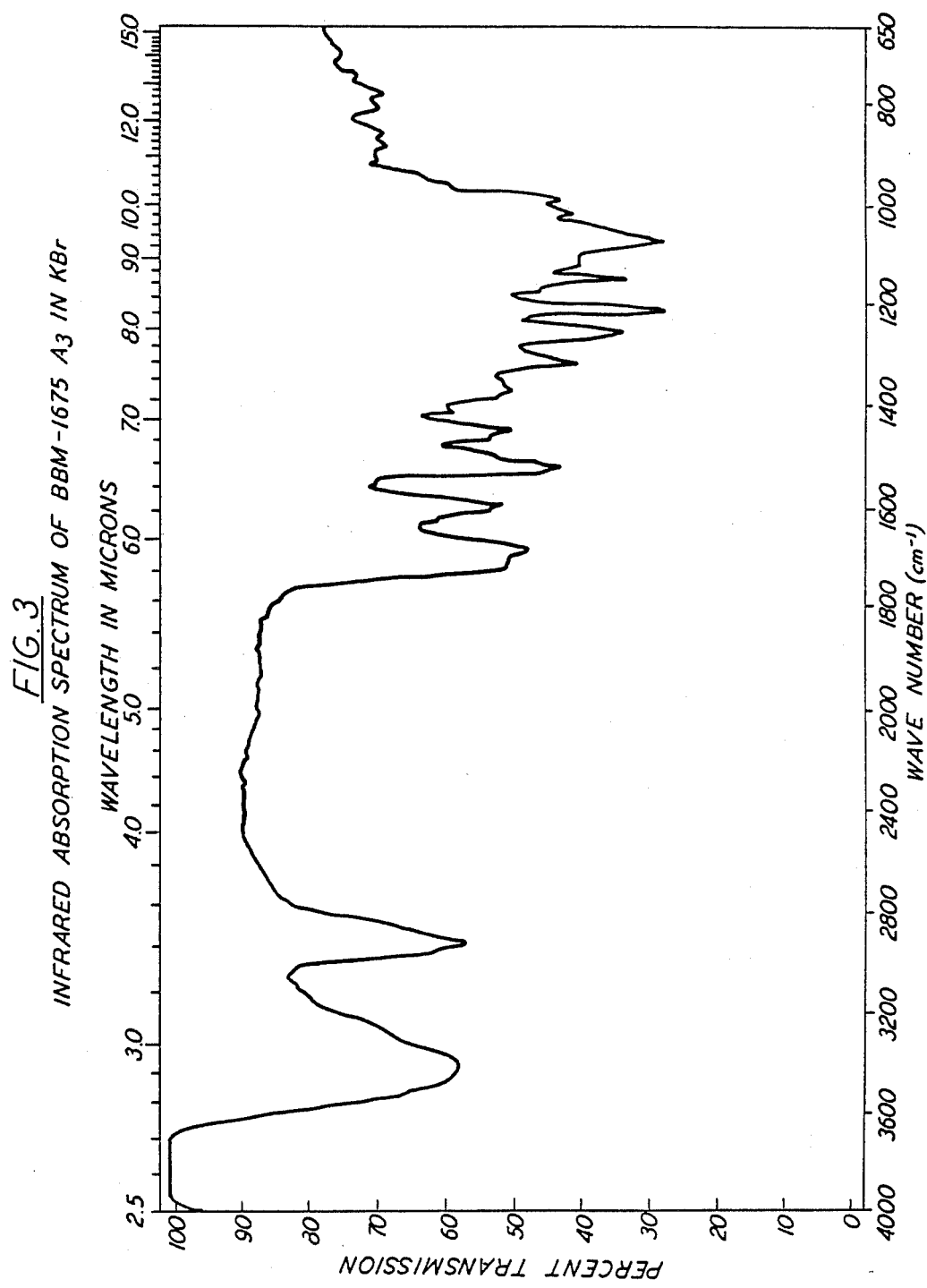
FIG. 3 shows the infrared absorption spectrum of BBM-1675 $A_3$ (KBr pellet).
Figure 4:
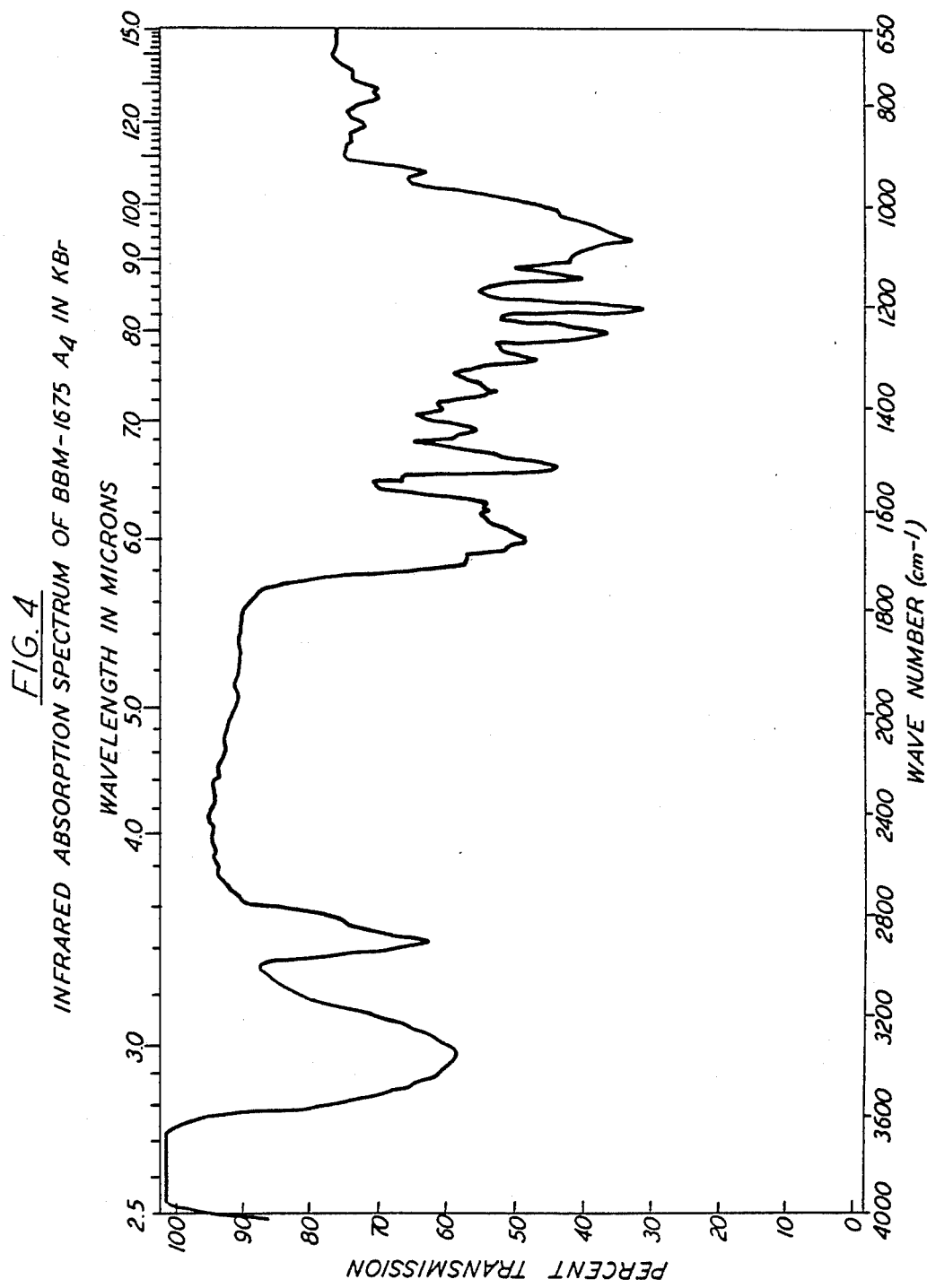
FIG. 4 shows the infrared absorption spectrum of BBM-1675 $A_4$ (KBr pellet).
Figure 5:
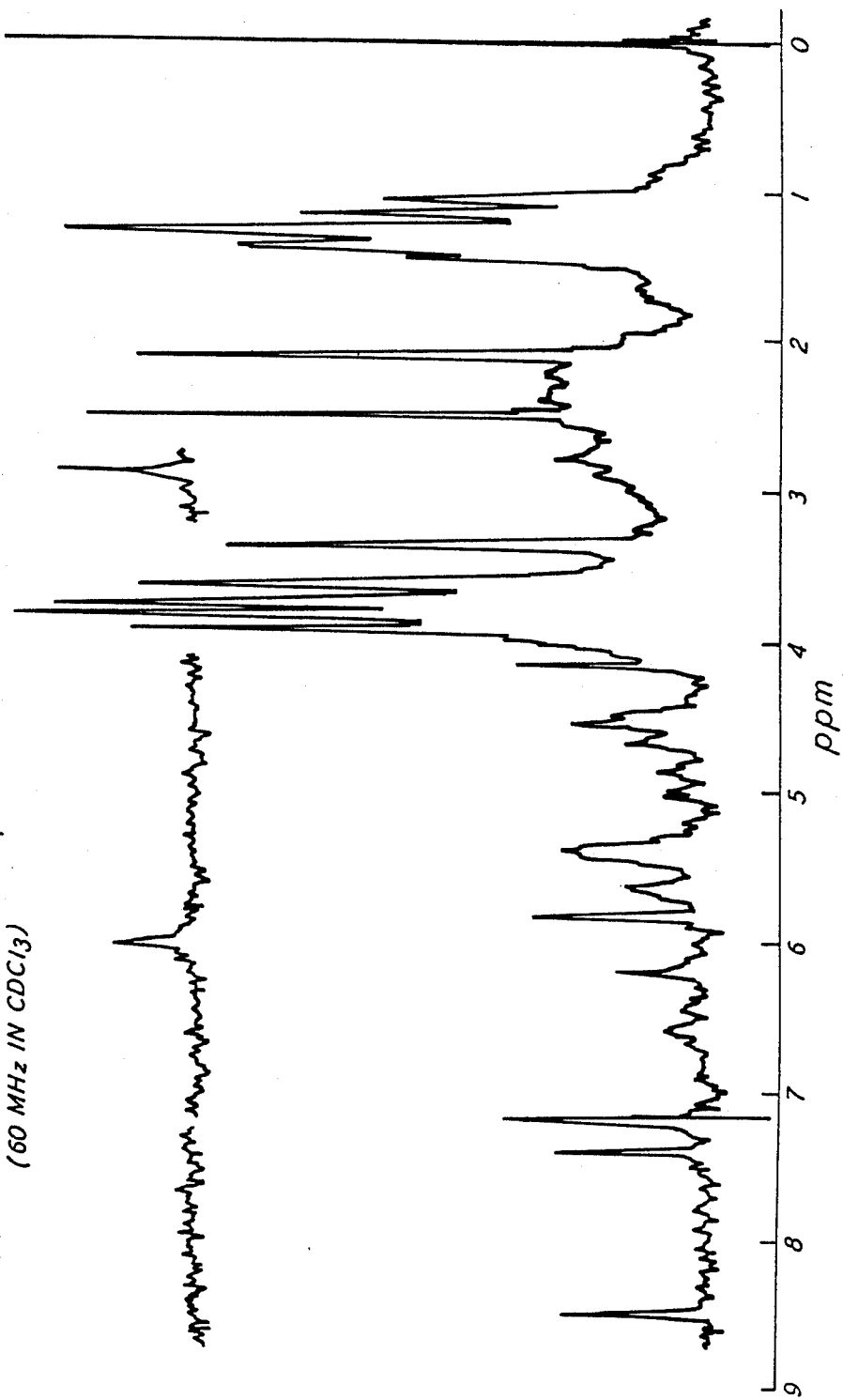
FIG. 5 shows the proton magnetic resonance spectrum of partially purified BBM-1675 $A_1$ in CDCl$_3$ (60 MHz).
Figure 6:
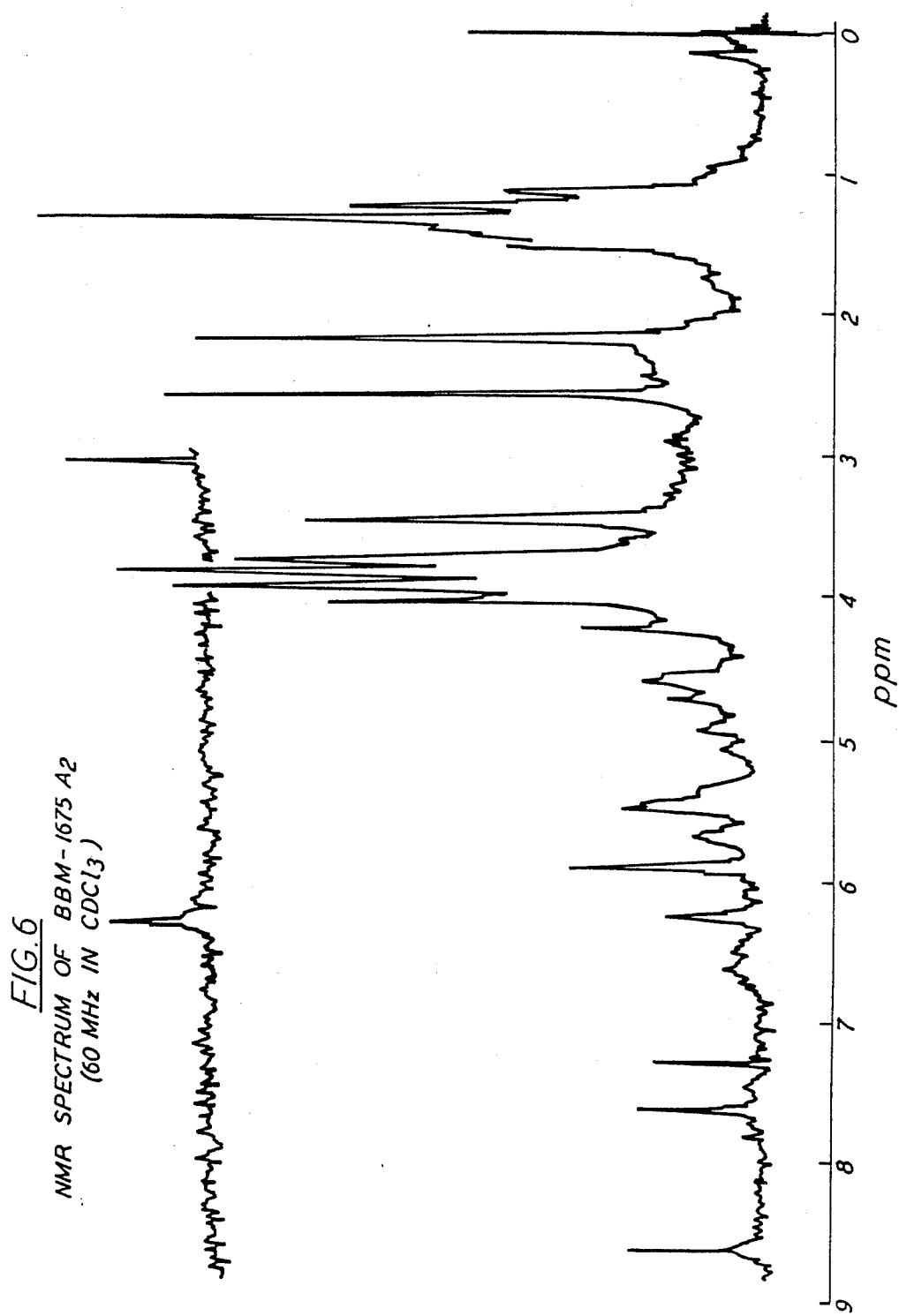
FIG. 6 shows the proton magnetic resonance spectrum of partially purified BBM-1675 $A_2$ in CDCl$_3$ (60 MHz).
Figure 7:
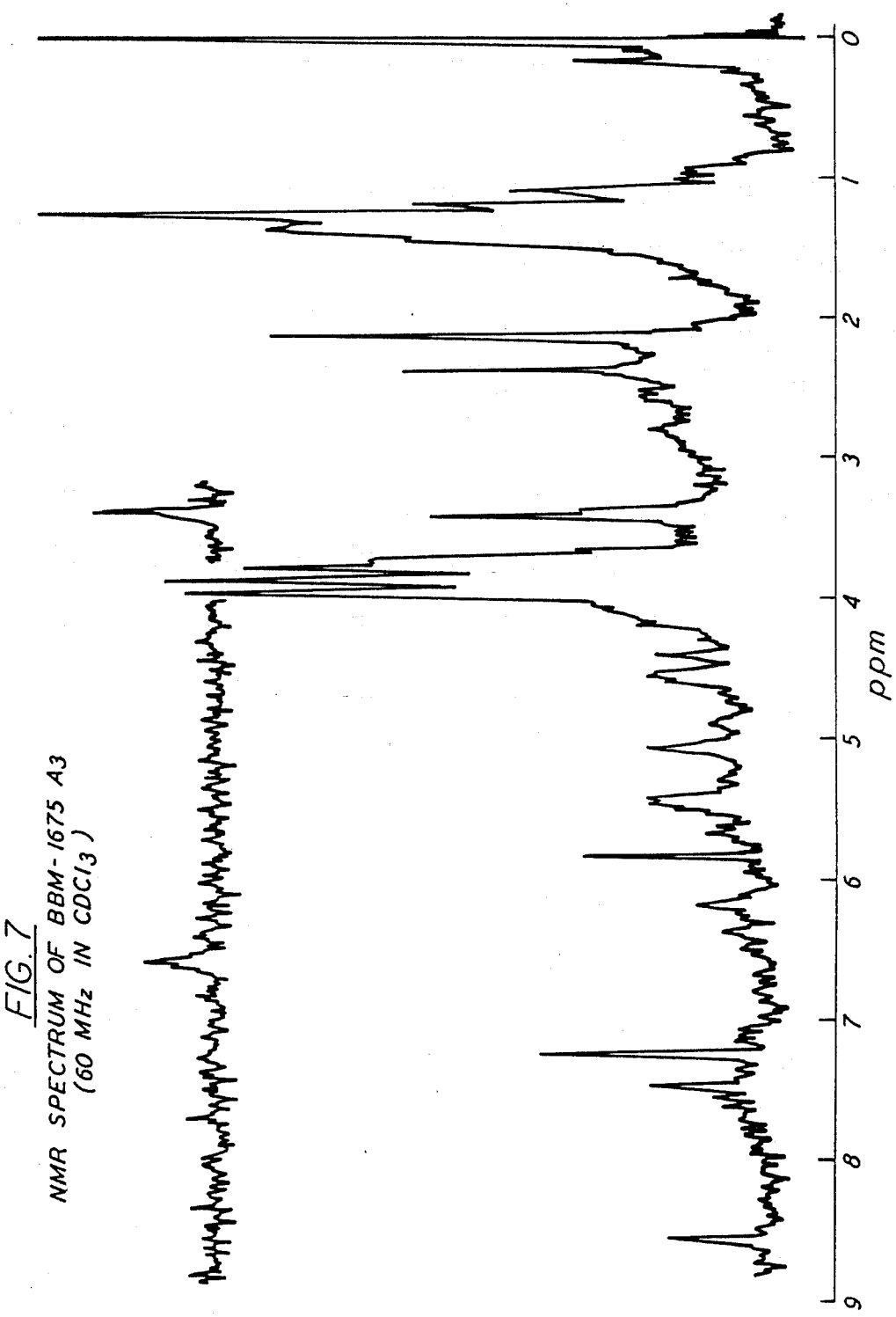
FIG. 7 shows the proton magnetic resonance spectrum of BBM-1675 $A_3$ in CDCl$_3$ (60 MHz).
Figure 8:
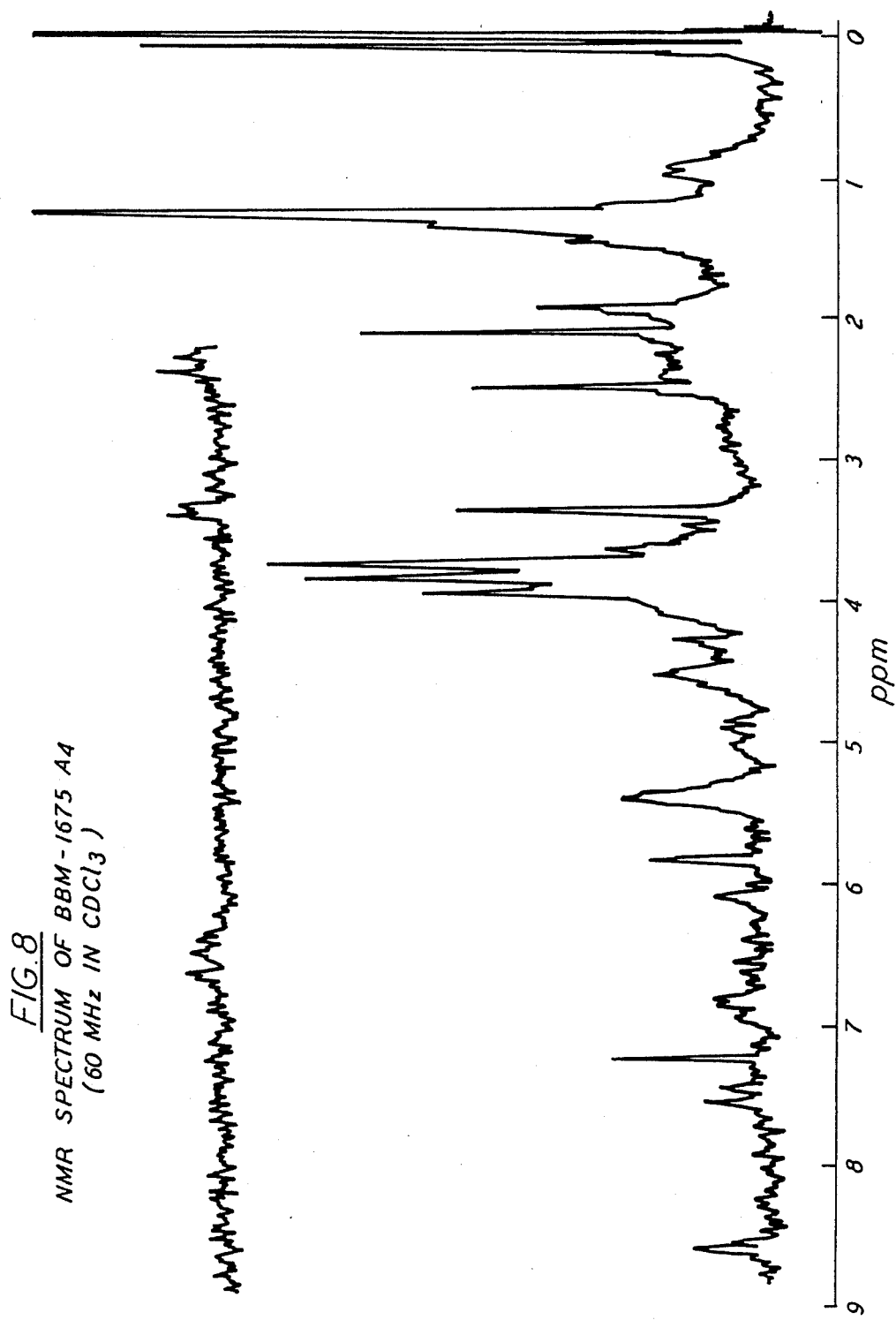
FIG. 8 shows the proton magnetic resonance spectrum of BBM-1675 $A_4$ in CDCl$_3$ (60 MHz).

This invention relates to a novel antitumor antibiotic complex designated herein as BBM-1675 and to its preparation by fermentation of certain strains of *Actinomadura verrucosospora*, most particularly *Actinomadura verrucosospora* strain H964-92 and a mutant thereof designated *Actinomadura verrucosospora* strain A1327Y. The above-mentioned parent strain was isolated from a soil sample collected at Pto Esperanza, Misiones, Argentina. A biologically pure culture of the organism has been deposited with the American Type Culture Collection, Washington, D.C. and added to its permanent collection of microorganisms as ATCC 39334. Subsequently, the mutant strain A1327Y was obtained by conventional nitrosoguanidine (NTG) treatment of strain H964-92 and was deposited with the American Type Culture Collection as ATCC 39638.

As in the case of many antibiotic-producing cultures, fermentation of *Actinomadura verrucosospora* strain H964-92 or strain A1327Y results in the production of a mixture or complex of component substances. Two major bioactive components, BBM-1675 $A_1$ and $A_2$, and four minor bioactive components, BBM-1675 $A_3$, $A_4$, $B_1$ and $B_2$, have been separated from the BBM-1675 complex produced during the fermentation process.

BBM-1675 and its components BBM-1675 $A_1$, $A_2$, $A_3$, $A_4$, $B_1$ and $B_2$ exhibit antimicrobial activity against a broad spectrum of microorganisms including especially gram-positive bacteria. The BBM-1675 complex and separated bioactive components thereof also exhibit phage inducing properties in lysogenic bacteria. Two of the components, BBM-1675 $A_1$ and $A_2$, have been submitted to in vivo screening against various mouse tumor systems and demonstrate inhibitory activity against L-1210 leukemia, P-388 leukemia, B16 melanoma and Lewis lung carcinoma. BBM-1675 $A_3$ and $A_4$ have been shown to exhibit activity against mouse P-388 leukemia. The complex and its bioactive components, therefore, may be used as antimicrobial agents or as antitumor agents for inhibiting mammalian tumors.

The Microorganism

The actinomycete Strain No. H964-92 was isolated from a soil sample and prepared by conventional procedures as a biologically pure culture for characterization. Strain H964-92 forms on the aerial mycelium short spore-chains which show straight, flexuous or hooked shapes. The spores are spherical or oval-shaped and have a warty surface. Aerial mycelium is poorly formed on most media. The aerial mass color is white which later turns to a pinkish shade, or further changes to a bluish color in some agar media. The color of substrate mycelium is colorless or pale pink. The growth temperature ranges from 15° C. to 43° C. The cell-wall amino acid composition and whole cell hydrolyzate sugar components show that strain H964-92 belongs to cell wall Type III$_B$. The menaquinone was identified as MK-9(H$_6$).MK-9(H$_8$).

Based on the major morphological, cultural and physiological characteristics along with the chemical cell-wall composition characteristics, strain H964-92 can be classified as belonging to the genus *Actinomadura*.

Although the original strain H964-92 gave only moderate growth and bore scant aerial mycelia, a variant showing good growth and improved aerial mycelium formation was obtained by NTG (nitrosoguanidine) treatment of H964-92. The variant, designated strain A1327Y, facilitated further taxonomical investigation and was subsequently identified as *Actinomadura verrucosospora*.

Methods

The media and procedures used for examining cultural characteristics and carbohydrate utilization were those recommended by the International Streptomyces Project (*Intl. J. Syst. Bacteriol.* 16: 313-340, 1966). Additional media described by S. A. Waksman (*The Actinomycetes*, Vol. 2) and G. M. Lvedemann (*Intl. J. Syst. Bacteriol.* 21: 240-247, 1971) were also used. The cell wall-amino acid composition and whole cell hydrolyzate sugar components were analyzed according to the methods described by Becker, et al. in *Appl. Microbiol.* 13: 236-243, 1965 and by Lechevalier and Lechevalier in *The Actinomycetes*, Ed. H. Prauser, Jena, Gustav Fischer Verlag, pp. 393-405, 1970, respectively. The menaquinone was identified by mass spectral analysis according to the procedures of Collins et al. in *J. Gen. Microbiol.* 100: 221-230, 1977, and the menaquinone composition was represented based on the system described by Yamada et al. in *J. Gen. Appl. Microbiol.* 23: 331-335, 1977.

Morphology

Strain H964-92 forms both substrate and aerial mycelia. The substrate mycelium is long, branched and not fragmented into short filaments. In the aerial mycelium, short spore-chains are formed monopodially or at the hyphal tip. Whorl-like branches of spore-chain are also observed nearby the hyphal tip. These spore-chains contain 2 to 10 spores in a chain and are straight, flexuous or hooked in shape. The spores have a warty surface and are spherical to elliptical (0.5-0.6×0.6-1.4 μm) in shape with rounded or pointed ends. After maturation each spore is often separated with empty sheath. Motile spores, sporangia or sclerotic granules are not seen in any media examined.

Cultural and Physiological Characteristics

Growth of strain H964-92 is poor to moderate in both chemically defined media and natural organic media. Formation of aerial mycelium is generally poor but is moderate in oat meal agar (ISP No. 3 medium), inorganic salts-starch agar (ISP No. 4 medium) and Bennett's agar. Spontaneous variants which lack aerial mycelium occur at high frequency. The color of aerial mycelium is white which later turns to pale pink in oat meal agar, inorganic salts-starch agar and glycerol-asparagine agar (ISP No. 5 medium). The aerial mass color further changes to a bluish color after long incubation (5 months) in oat meal agar, glycerol-asparagine agar and tyrosine agar. The color of substrate mycelium is colorless to yellowish in Czapek's agar, tyrosine agar, yeast extract-malt extract agar (ISP No. 2 medium), peptone-yeast extract-iron agar (ISP No. 6 medium) and Bennett's agar, and is a pinkish color in glucose-asparagine agar and glycerol-asparagine agar. Melanoid and other diffusible pigments are not produced. A variant No. A1327Y, which was obtained from the original strain, forms predominantly pale blue aerial mycelium and bears abundant aerial spore mass.

Strain H964-92 grows at 15° C., 28° C., 37° C. and 43° C., but not at 10° C. or at 47° C. It is sensitive to NaCl at 7%, and resistant to lysozyme at 0.01%.

The cultural and physiological characteristics of the producing strain are shown in Tables 1 and 2, respectively. The utilization of carbon sources is shown in Table 3.

TABLE 1

Cultural Characteristics of Strain H964-92 (original strain ATCC 39334 and variant A1327Y)

| | Strain No. H964-92 | | *Actinomadura verrucosospora* KCC A-0147 |
|---|---|---|---|
| | Original Strain (ATCC 39334) | Variant No. A1327Y | |
| Tryptone-yeast extract agar (ISP No. 1) | G: abundant, floccose, sedimented and not pigmented | moderate, floccose, sedimented and not pigmented | moderate, floccose, sedimented and not pigmented |
| Sucrose-nitrate agar (Czapek's agar) | G: moderate | poor | poor |
| | R: colorless | colorless | colorless |
| | A: scant, light gray (264), to pale pink (7) | no or scant; pinkish white (9) | no or scant; pale blue (185) |
| | D: none | none | none |
| Glucose-asparagine agar | G: moderate | poor | poor |
| | R: white (263) to deep yellowish pink (27) | colorless | colorless |
| | A: no or very scant; pale pink (7) | no or very scant; white | no or very scant; white |

TABLE 1-continued

Cultural Characteristics of Strain H964-92
(original strain ATCC 39334 and variant A1327Y)

| | | Strain No. H964-92 | | Actinomadura verrucosospora KCC A-0147 |
|---|---|---|---|---|
| | | Original Strain (ATCC 39334) | Variant No. A1327Y | |
| Glycerol-asparagine agar (ISP No. 5) | D:<br>G:<br>R:<br><br>A: | none<br>poor to moderate<br>colorless to light yellowish pink (28)<br>poor; light yellowish pink (28), after 5 months light bluish gray (190) | none<br>moderate<br>light yellowish pink (28)<br><br>moderate; white to light pink (4) | none<br>moderate<br>light yellowish pink (28) to deep yellowish pink (27)<br>moderate; white to strong pink (2) |
| Inorganic salts-starch agar (ISP No. 4) | D:<br>G:<br>R:<br>A: | none<br>abundant<br>yellowish white (92)<br>abundant; light pink (4) to pinkish gray (10) | none<br>moderate<br>light yellowish pink (28)<br>moderate; light bluish gray (190) | none<br>moderate<br>light yellowish pink (28)<br>abundant; pale blue (185) |
| Tyrosine agar (ISP No. 7) | D:<br>G:<br>R:<br>A: | none<br>moderate<br>yellowish white (92)<br>poor; light yellowish pink (28), very later (5 months) partially light bluish gray (190) | none<br>moderate<br>strong yellowish pink (26)<br>moderate; white to light pink (4) | none<br>moderate<br>strong yellowish pink (26)<br>moderate; white to light pink (4) |
| Nutrient agar | D:<br>G:<br>R:<br>A: | none<br>poor to moderate<br>pale yellow (89)<br>none | none<br>poor<br>colorless to pale pink (7)<br>none | none<br>poor<br>colorless to pale pink (7)<br>none |
| Yeast extract-malt extract agar (ISP No. 2) | D:<br>G:<br>R:<br>A: | none<br>abundant<br>pale yellow (89)<br>poor; white (263) | none<br>abundant<br>strong yellowish pink (26)<br>poor; white to pale pink (7) | none<br>abundant<br>strong yellowish pink (26)<br>poor; white to pale pink (7) |
| Oat meal agar (ISP No. 3) | D:<br>G:<br>R:<br>A: | none<br>moderate<br>colorless to pale pink (7)<br>poor; pinkish white (9) to light bluish gray (190) | none<br>poor<br>pale yellowish pink (31)<br>very scant; vivid pale blue (184) | none<br>poor<br>pale yellowish pink (31)<br>very scant; vivid pale blue (184) |
| Bennett's agar | D:<br>G:<br>R:<br>A: | none<br>abundant<br>grayish yellow (90)<br>moderate; white (263) to yellowish white (92) | none<br>abundant<br>strong yellowish pink (26)<br>moderate; pale yellowish pink (31) and bluish white (189) | none<br>abundant<br>strong yellowish pink (26)<br>none |
| Peptone-yeast extract-iron agar (ISP No. 6) | D:<br>G:<br>R:<br>A:<br>D: | none<br>moderate<br>colorless<br>none<br>none | none<br>abundant<br>colorless<br>none<br>none | none<br>abundant<br>colorless<br>none<br>none |

*Observed after incubation at 37° C. for 3 weeks.
**Abbreviation: G = Growth; R = Reverse color; A = Aerial mycelium; D = Diffusible pigment
***Color and number in parenthesis follow the color standard in *Kelly, K. L. & D. B. Judd; ISCC-NBS color-name charts illustrated with Centroid Colors. U.S. Dept. of Comm. Cir. 553, Washington, D.C., Nov., 1975*.

TABLE 2

Physiological Characteristics of Strain H964-92

| Test | Response | Method and Medium |
|---|---|---|
| Range of temperature for growth | Maximal growth at 28° C. to 37° C. Moderate at 20° C. and 43° C. No growth at 10° C. | Bennett's agar |
| Gelatin liquefaction | Liquefied | Glucose-peptone gelatin medium |
| Starch hydrolysis | Hydrolyzed | Starch agar plate |
| Reactions in skimmed milk | Not coagulated and completely peptonized | Difco skimmed milk |
| Formation of melanoid | Not produced | Tyrosin agar, peptone-yeast- |

TABLE 2-continued
Physiological Characteristics of Strain H964-92

| Test | Response | Method and Medium |
|---|---|---|
| pigment | | iron agar and tryptone-yeast extract broth. |
| Nitrate reduction | Not reduced | Czapek's glucose-nitrate broth and glucose-yeast extract-nitrate broth |
| Resistance to NaCl | Growth at 5% or less. No growth at 7%. | Tryptone-yeast extract agar |
| Lysozyme | Resistant. Growth at 0.01% or less. No growth at 0.1%. | Tryptone-yeast extract agar |
| pH | Growth in 5.0 to 9.5. No growth at 4.5 and 10.0. | Tryptone-yeast extract agar |

TABLE 3
Utilization of Carbon Sources

| | Strain No. H964-92 | | Actinomadura verrucosospora KCC A-0147 |
|---|---|---|---|
| | Original strain | Variant No. A1327Y | |
| Glycerol | + | + | + |
| D(−)-Arabinose | − | − | − |
| L(+)-Arabinose | + | + | + |
| D-Xylose | + | + | + |
| D-Ribose | + | − | − |
| L-Rhamnose | + | + | + |
| D-Glucose | + | + | + |
| D-Galactose | − | − | − |
| D-Fructose | + | + | + |
| D-Mannose | − | − | − |
| L(−)-Sorbose | − | − | − |
| Sucrose | + | + | + |
| Lactose | − | − | − |
| Cellobiose | + | + | + |
| Melibiose | − | − | − |
| Trehalose | + | + | + |
| Raffinose | − | − | − |
| D(+)-Melezitose | − | − | − |
| Soluble starch | + | + | + |
| Cellulose | + | + | + |
| Dulcitol | − | − | − |
| Inositol | + | − | − |
| D-Mannitol | + | + | + |
| D-Sorbitol | − | − | − |
| Salicin | − | − | − |

Observed after incubation at 28° C. for 3 weeks
Basal medium: Pridham-Gottlieb inorganic medium

Cell-Wall Composition and Whole Cell Sugar Components

Purified cell-wall of strain H964-92 contains mesodiaminopimelic acid but lacks glycine. The whole cell hydrolyzate shows the presence of madurose (3-O-methyl-D-galactose), glucose and ribose. The cell-wall amino acid and whole cell sugar components indicate that strain H964-92 is placed in cell-wall Type $III_B$. Two major components of menaquinone were identified as MK-9($H_6$) and MK-9($H_8$).

Taxonomic Position of Strain H964-92

Strain H964-92 has the following major characteristics: (1) Aerial spore-chains: short, straight, flexuous or hooked in shape. (2) Spores: warty surface. (3) Aerial mycelium: pinkish or bluish color. (4) Substrate mycelium: pinkish in some media. (5) Diffusible pigment: none. (6) Mesophile. (7) Cell-wall Type $III_B$. (8) Menaquinone system: MK-9($H_6$) and MK-9($H_8$).

These major characteristics indicate that strain H964-92 is placed in the genus Actinomadura. Early species of the genus Actinomadura were isolated from mammals. Some strains were also obtained from plant materials. However, many of the new species proposed recently were isolated from soil. According to the numerical taxonomy and review of the Actinomadura and related actinomycetes by Goodfellow et al. in *J. Gen. Microbiol.* 112: 95–111 (1979), most Actinomadura species of soil origin are classified into Cluster No. 7 among the 14 clusters described. Strain No. H964-92 is most related to the species of Cluster 7. Nonomura and Ohara in *J. Ferment. Technol.* 49: 904–912 (1971) reported five saprophytic species of the genus Actinomadura and Nonomura [*J. Ferment. Technol.* 52: 71–77 (1974)] and Preobrazhenskaya et al. [*Actinomycetes and Related Organisms* 12: 30–38 (1977)] published the keys for identification and classification of the Actinomadura species. As a result of comparison with the descriptions of 30 species including organisms disclosed in patents, strain H964-92 appears most similar to *Actinomadura coerulea* described in the Preobrazhenskaya et al. reference above and to *Actinomadura verrucosospora* described in the Nonomura references cited above.

Strain No. H964-92 was directly compared with *A. verrucosospora* strain KCC A-0147 and was found to be closely related to *A. verrucosospora* in the morphological, cultural and physiological characteristics. Thus, strain H964-92 is classified as a new strain of *Actinomadura verrucosospora*.

It is to be understood that for the production of BBM-1675, the present invention, though described in detail with reference to the particular strain *Actinomadura verrucosospora* strain H964-92 (ATCC 39334) and the mutant strain thereof designated strain A1327Y (ATCC 39638), is not limited to these microorganisms or to microorganisms fully described by the cultural characteristics disclosed herein. It is specifically intended that the invention embrace strain H964-92 and all natural and artificial BBM-1675-producing variants and mutants thereof.

Antibiotic Production

The BBM-1675 antibiotics of the present invention may be prepared by cultivating a BBM-1675-producing strain of *Actinomadura verrucosospora*, preferably a strain of *Actinomadura verrucosospora* having the identifying characteristics of ATCC 39334 or ATCC 39638, or a mutant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as glycerol, L(+)-arabinose, D-xylose, D-ribose, L-rhamnose, D-glucose, D-fructose, sucrose, cellobiose, soluble starch, D-mannitol or inositol. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of the BBM-1675 antibiotics can be effected at any temperature conducive to satisfactory growth of the producing organism, e.g. 15°–45° C., and is conveniently carried out at a temperature of around 27°–32° C. Ordinarily, optimum production is obtained after incubation periods of from about 68–180 hours, depending on whether shake-flask, stir-jar or tank fermentation is employed. When tank fermentation is to be carried out, it is desirable to produce a vegetative inoculum in a nutrient broth by inoculating the broth culture with a slant or soil culture or a lyophilized culture of the producing organism. After obtaining an active inoculum in this manner, it is transferred aseptically to the fermentation tank medium. Antibiotic production may be monitored by the paper disc-agar diffusion assay using *Staphylococcus aureus* 209P as the test organism.

Isolation and Purification

When fermentation is complete, the BBM-1675 complex may be obtained from the broth by conventional isolation procedures, e.g. solvent extraction. Thus, for example, the whole broth may be separated by filtration or centrifugation into mycelial cake and broth supernatant. Antibiotic in the mycelial cake may be recovered by suspending the cake in methanol, filtering off insoluble materials and concentrating the methanolic extract. Activity in the broth supernatant may be recovered by extraction with n-butanol. The above-mentioned n-butanol and methanol extracts may then be combined and evaporated azeotropically to an aqueous solution which deposits most of the antibiotic activity as an oily solid. The solid may then be dissolved in methanol and the solution filtered. Filtrate is concentrated and added to a mixture of ethyl acetate and water. The resulting organic extract contains the crude BBM-1675 complex which may be precipitated from solution by addition of an antisolvent such as n-hexane.

The crude BBM-1675 complex is a mixture of several components including two major bioactive components, BBM-1675 $A_1$ and $A_2$, and four minor bioactive components, BBM-1675 $A_3$, $A_4$, $B_1$ and $B_2$. These bioactive components may be separated and purified by conventional chromatographic procedures. In one procedure the crude BBM-1675 complex is first dissolved in methanol and purified by Sephadex LH-20 column chromatography using methanol as the eluting solvent. This partially purified complex may then be chromatographed on a silica gel column and eluted in a stepwise manner using chloroform plus an increasing concentration of methanol to provide BBM-1675 $A_1$, a mixture of BBM-1675 $A_2$, $A_3$ and $A_4$ and a mixture of BBM-1675 $B_1$ and $B_2$. The $A_1$ component may be further purified by Sephadex LH-20 column chromatography using methanol as the eluting solvent. The mixture of $A_2$, $A_3$ and $A_4$ may be separated by chromatography on a column of Bondapak $C_{18}$ (Waters Associates, Inc.) using increasing concentrations of aqueous acetonitrile as the eluant. The mixture of $B_1$ and $B_2$ components may be separated by silica gel column chromatography using a mixture of chloroform and methanol as the eluting solvent. Further details of the preferred chromatographic separation procedures are provided in the examples which follow.

Physico-chemical Properties of BBM-1675 Components

The six bioactive components of BBM-1675 complex are distinguishable from each other by two TLC systems as shown in the following Table.

TABLE 4

| Component | TLC of BBM-1675 Components Rf Values | |
|---|---|---|
| | $SiO_2$ $CHCl_3—CH_3OH$ (5:1 v/v) | *Silanized $CH_3CN—H_2O$(75:25 v/v) |
| BBM-1675 $A_1$ | 0.74 | 0.18 |
| BBM-1675 $A_2$ | 0.71 | 0.21 |
| BBM-1675 $A_3$ | 0.72 | 0.28 |
| BBM-1675 $A_4$ | 0.71 | 0.78 |
| BBM-1675 $B_1$ | 0.63 | 0.23 |
| BBM-1675 $B_2$ | 0.60 | 0.16 |

*$C_{18}$ reverse phase silica gel

Separation of BBM-1675 $A_2$, $A_3$ and $A_4$ was difficult by ordinary phase TLC systems but could be achieved by a reverse phase TLC.

The individual BBM-1675 components show solubility and color reactions similar to each other. For example, they are soluble in chloroform, ethyl acetate, acetone, ethanol and methanol, slightly soluble in benzene and water, and insoluble in n-hexane and carbon tetrachloride. They give positive reactions with ferric chloride, Ehrlich and Tollen's reagents but negative responses in Sakaguchi, ninhydrin and anthrone tests.

Characteristic physico-chemical properties of BBM-1675 components are shown in the Table 5 below.

TABLE 5

| | Physico-Chemical Properties of BBM-1675 Components | | | | | |
|---|---|---|---|---|---|---|
| | BBM-1675 $A_1$ | $A_2$ | $A_3$ | $A_4$ | $B_1$ | $B_2$ |
| Melting point (dec) | 156–158° C. | 147–149° C. | 125–127° C. | 123–126° C. | 159–161° C. | 156–159° C. |
| $[\alpha]_D^{27}$ (c. 0.5, $CHCl_3$) | −191° | −179.4° | −161° | −176° | −171° | −122° |
| Anal. Found (%), C | 51.52 | 53.81 | 55.00 | 53.67 | | |
| H | 5.81 | 6.31 | 6.52 | 6.35 | | |
| N | 4.02 | 3.82 | 3.57 | 3.45 | | |
| (by difference) O | 38.65 | 36.06 | 34.91 | 36.53 | | |
| UV $\lambda_{max}$ nm($E_{1cm}^{1\%}$) in $CH_3OH$ | 253 (325) | 253 (281) | 253 (286) | 253 (257) | 253 (225) | 248 (212) |

TABLE 5-continued

| | Physico-Chemical Properties of BBM-1675 Components | | | | | |
|---|---|---|---|---|---|---|
| | BBM-1675 $A_1$ | $A_2$ | $A_3$ | $A_4$ | $B_1$ | $B_2$ |
| | 282 (195) | 282 (172) | 282 (158) | 282 (153) | 282 (140) | 279 (141) |
| | 320 (143) | 320 (128) | 320 (122) | 320 (117) | 320 (104) | 318 (103) |
| in 0.01 N HCl—CH$_3$OH | 253 (323) | 253 (276) | 253 (287) | 253 (258) | 253 (225) | 248 (210) |
| | 282 (192) | 282 (167) | 282 (160) | 282 (155) | 282 (140) | 279 (140) |
| | 320 (144) | 320 (128) | 320 (126) | 320 (118) | 320 (105) | 318 (103) |
| in 0.01 N NaOH—CH$_3$OH | 252 (325) | 252 (289) | 252 (280) | 252 (266) | 252 (236) | 248 (233) |
| | 283 (172) | 283 (171) | 283 (162) | 283 (160) | 282 (141) | 278 (150) |
| | 318 (136) | 318 (122) | 318 (120) | 318 (118) | 318 (105) | 318 (110) |
| Mol. wt. (approximate value) (Gel HPLC, Finepak GEL-101) | 1,300 | 1,100 | 1,100 | 1,400 | | |

The UV absorption maxima of BBM-1675 components were observed at 253, 282 and 320 nm, which did not shift in acidic or alkaline solution. The IR and PMR spectra of BBM-1675 $A_1$, $A_2$, $A_3$ and $A_4$ are shown in FIG.'s 1-4 and FIG.'s 5-8 respectively. The 360 MHz PMR of BBM-1675 $A_1$ indicated one acetyl (δ: 2.11 ppm), one N—CH$_3$(2.52 ppm), four OCH$_3$(3.42, 3.80, 3.88 and 3.98 ppm) and one exomethylene (4.57 and 5.48 ppm) groups, along with two aromatic (7.50 and 8.59 ppm) and one NH (11.79 ppm) protons. The CMR spectrum of BBM-1675$A_1$ exhibited 55 carbon signals including a triple intensity signal (δ: 56.0 ppm, OCH$_3$). The molecular formula of BBM-1675$A_1$ is deduced to be $C_{57}H_{72}N_4O_{32}$ based on proton and $^{13}C$ NMR spectra, micronalysis and molecular weight determination by HPLC and SIMS (secondary ion mass spectrometry).

Structural Study of BBM-1675 $A_1$

Upon treatment with 0.5N HCl—CH$_3$OH at room temperature, BBM-1675$A_1$ loses its bioactivity and affords a lipophilic chromophore substance (compound I) along with several unidentified fragments. Compound I shows UV absorption similar to that of parent antibiotic suggesting that compound I retains the chromophoric structure of BBM-1675$A_1$. Two other chromophoric fragments related to compound I are obtained by alkaline hydrolysis of BBM-1675$A_1$: hydrolysis with 0.05N KOH—CH$_3$OH at 55° C. for one hour yields compound II having UV absorption maxima at 252, 284, 297 (shoulder) and 322 nm, while the reaction in 1N KOH—CH$_3$OH affords an acidic chromophore substance designated compound III. Physico-chemical properties of compounds I, II and III are summarized in Table 6 below.

chemical transformation. The $^{13}C$ and proton NMR indicated the presence of four OCH$_3$, one =CH$_2$, seven

two >C=O and one >NH groups in compound II. The NMR spectra of compound III was similar to those of II, differing only in the absence of one of the four OCH$_3$ groups observed for compound II. This difference, together with the acidic nature of compound III, suggested that compound II is a methyl ester of compound III. When heated under reflux with 1N methanolic KOH, compound II was quantitatively converted to compound III, while compound III was converted to compound II by treatment with diazomethane. Treatment of compound II with NaBH$_4$ in C$_2$H$_5$OH gave a reduction product (compound IV, M+: m/z 267) which showed a —CH$_2$OH group in the NMR in place of the —COOH$_3$ group of compound II. Upon hydrogenation over palladium on charcoal, compound II afforded a dihydroderivative (compound V, M+: m/z 297). The proton NMR spectrum of compound V exhibited a new doublet methyl signal and the absence of the exomethylene group present in compound II. Furthermore, one of the OCH$_3$ groups appeared at higher field (δ: 3.50 ppm) in compound V. These results indicated the presence of a

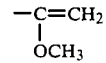

TABLE 6

| | Properties of Compounds I, II and III | | |
|---|---|---|---|
| | Compound I | Compound II | Compound III |
| M.p. | 82-83° C. | 133° | 253-255° C. |
| $[\alpha]_D^{29}$ (c 0.2 CHCl$_3$) | −100° | 0 | 0 |
| Molecular formula | $C_{21}H_{31}NO_{10}$ | $C_{14}H_{17}NO_6$ | $C_{13}H_{15}NO_6$ |
| UV $\lambda_{max}^{CH_3OH}$ nm (t) | 244 (21,850) | 252 (26,600) | 248 (26,900) |
| | 276 (9,400) | 283 (11,200) | 295 (14,400) |
| | 318 (6,300) | 297 (sb8,800) | 310 (13,500) |
| | | 322 (11,700) | |
| MS m/z | 457 (M+) | 295 (M+) | 281 (M+) |
| | 425 | 280 | 263 |
| | 341 | 263 | 236 |
| | 281 | 251 | 222 |
| | 264 | 248 | 218 |
| TLC (Xylene-*MEK—CH$_3$OH = 5:5:1 v/v) | Rf 0.58 | 0.66 | 0.13 |

*MEK = methyl ethyl ketone

Structural information about compounds II and III was provided from the following spectral data and group in compound II which was reduced by hydrogenation to

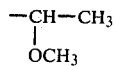

group in compound V. Compound II was heated with 1.5N methanolic hydrogen chloride at 80° C. for 3 hours and the hydrolyzate chromatographed on a silica gel column to afford a weakly basic compound (compound VI, M+: m/z 211). The IR spectrum and physico-chemical properties indicated that compound VI contained an NH₂ group. Compound VI was identified as methyl 4,5-dimethoxy-anthranilate by comparative IR and NMR studies with an authentic sample. Consequently, the structures of compounds II–VI were determined as shown below.

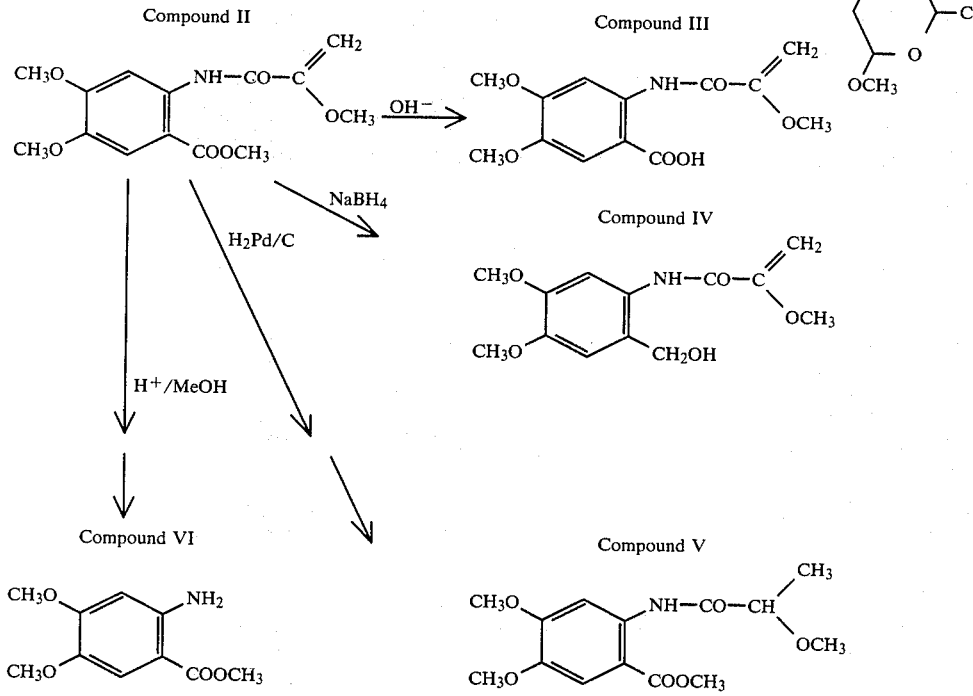

Upon treatment with 0.05N KOH—CH₃OH at 55° C., compound I was split into a new chromophoric fragment (compound VII, C₁₅H₂₁NO₇, M+: m/z 327) and a sugar (compound VIII). The NMR spectrum of VII exhibited one singlet C—CH₃ and two high-field OCH₃ groups in addition to three low-field OCH₃ and two aromatic protons commonly observed for compounds II, V and VI. Further hydrolysis of VII with 1.5N methanolic hydrogen chloride gave compound VI which was identical with that previously obtained from II. After removal of VI, the hydrolyzate was treated with 2,4-dinitrophenylhydrazine to precipitate yellow solid which was identified as 2,4-dinitrophenylhydrazone of pyruvic acid. Thus, compound VII is methyl 4,5-dimethoxy-N-(2',2'-dimethoxypropionyl)anthranilate. Compound VIII did not show the molecular ion peak but did show the M—OCH₃ peak at m/z 131 in the mass spectrum in agreement with the molecular formula of C₇H₁₄O₄. The NMR spectrum indicated 2,6-dideoxyhexopyranose structure for compound VIII. The assignment was supported by the ¹³C—NMR of compound I which gave rise to one C—CH₃, one —CH₂, three O—CH< and one anomeric carbon in addition to 15 carbon signals assignable to compound VII. The C₃ proton of the sugar appeared at low-field (δ: 5.39 ppm, octet) revealing that C₃—OH of the sugar was esterified by the carboxyl group of VII. The above results are summarized below:

Structures of Compound I, VII and VIII

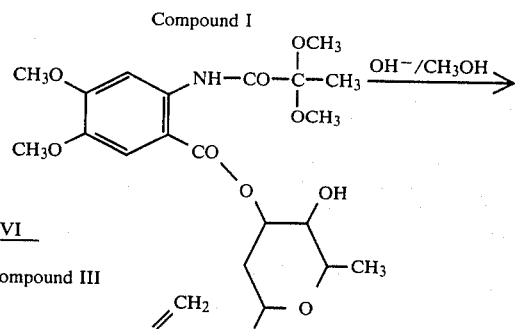

-continued
Structures of Compound I, VII and VIII

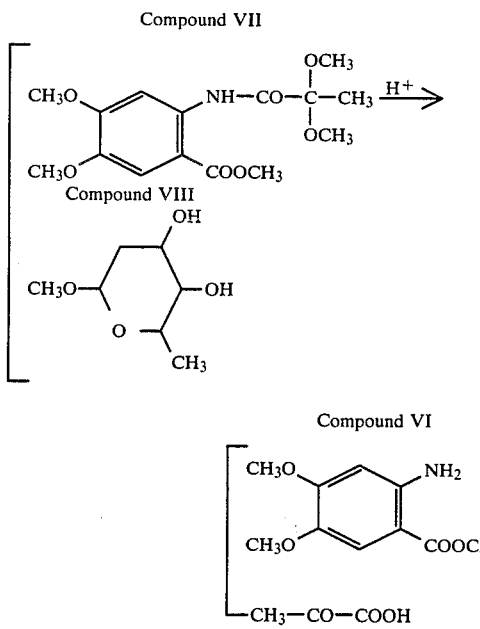

The molecular weight of compound I (457) accounts for about one-third of the entire molecule of BBM-1675A$_1$ (proposed formula $C_{57}H_{72}N_4O_{32}$; calc'd MW=1324). The partial structure of BBM-1675 A$_1$ is considered to be as follows:

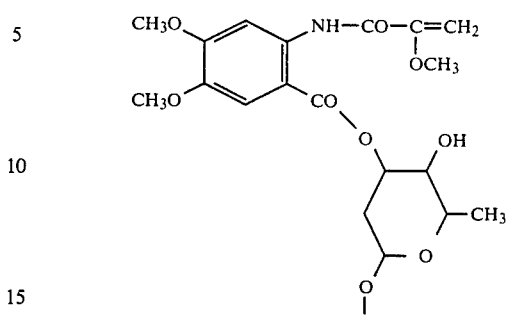

Subsequent to the U.S. filing date of parent application Ser. No. 495,231, it was discovered that components BBM-1675 A$_1$ and A$_2$ described above and produced according to Example 2 below were in fact not completely pure and that certain of the characterizing properties used to define such components were inaccurate. Following additional chromatographic purification procedures as described more fully in Examples 3 and 6 below, BBM-1675 A$_1$ and A$_2$ were isolated in more purified form and fully characterized as described below. Also, the elemental analysis data for components A$_3$ and A$_4$ was revised to show the presence of sulfur in these compounds and HPLC retention times were calculated for these two components. Summarized below are the revised physico-chemical properties of the BBM-1675 components.

Figure 9:
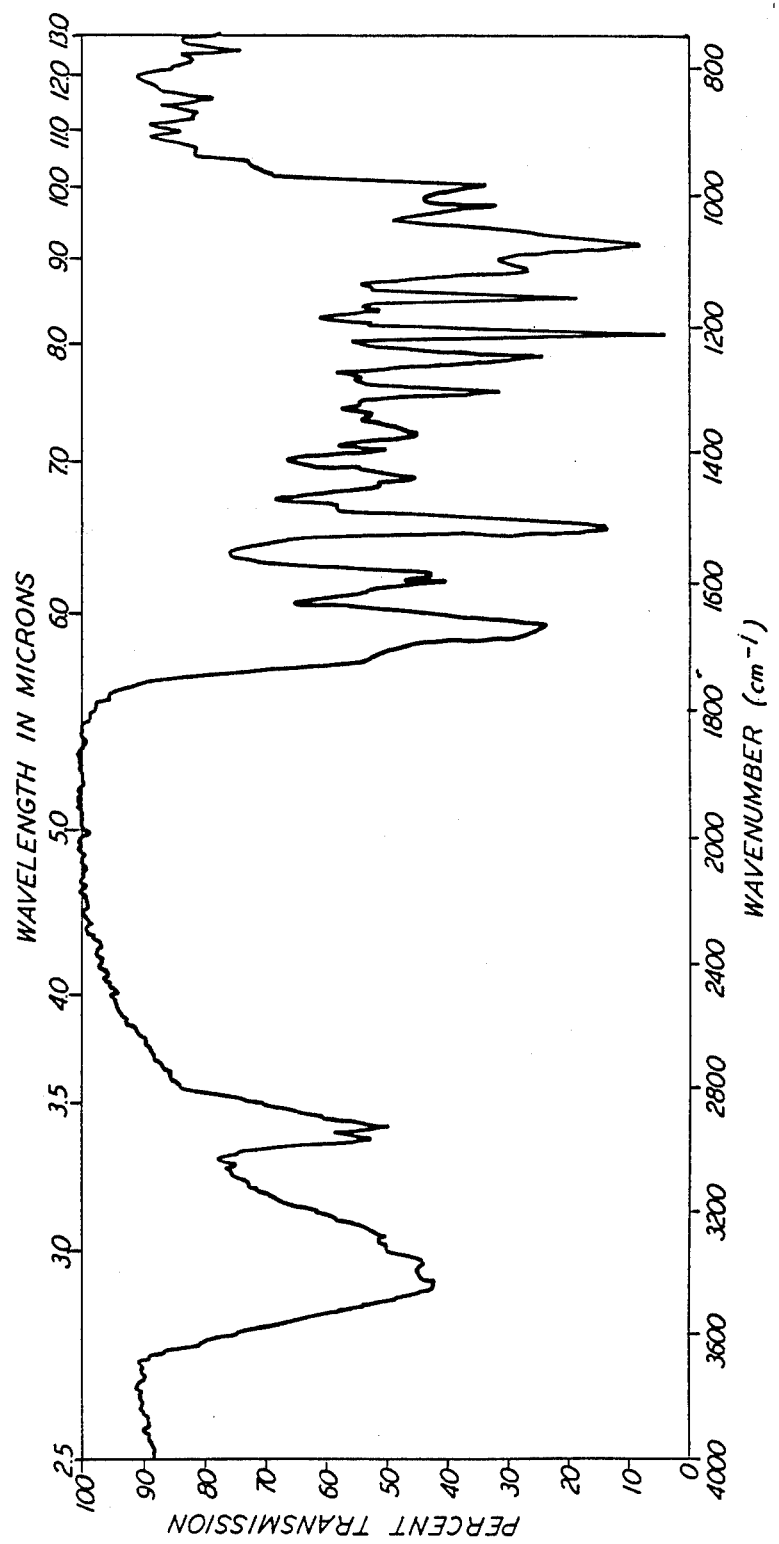
FIG. 9 shows the infrared absorption spectrum of purified BBM-1675 $A_1$ (KBr pellet).

| BBM-1675 A$_1$ | | | |
|---|---|---|---|
| Description: | | | white to pale yellow crystals; mp 156–158° (dec.) |
| Elemental analysis: | | | |
| Analysis 1 | Analysis 2 | | Average |
| C: 51.60% | C: 52.74% | | C: 52.17 |
| H: 6.31% | H: 5.99 | | H: 6.15 |
| N: 5.31% | N: 3.94% | | N: 4.63% |
| S: 8.47% | S: 9.71% | | S: 9.09% |
| O (by difference): 28.31% | O (by difference): 27.62% | | O (by difference): 27.96% |
| Ultraviolet absorption spectrum: | | | Instrument-Varian UV, Cary 219 Solvent - methanol Concentration - 0.01356 g/l |
| | $\lambda_{max}$(nm) | | absorptivities |
| | 320 | | 12.4 |
| | 280 | | sh (shoulder) |
| | 253 | | 25.1 |
| | 210 | | 25.5 |
| | | | No significant change with acid or base |
| Optical rotation: | | | Solvent - CHCl$_3$ $[\alpha]_D^{24°} = -207°$ (C = 0.0351) A second analysis showed the following optical rotation: $[\alpha]_D^{27°} = -191°$ (C = 0.5, CHCl$_3$). |
| Infrared absorption spectrum: | See FIG. 9 | | |
| | | | Major absorption bands (KBr): 985, 1015, 1070, 1110, 1150, 1210, 1250, 1308, 1380, 1405, 1446, 1520, 1592, 1608, 1668, 1715, 2920, 2960, 3360, 3440, cm$^{-1}$ |
| Mass spectra: | | | Instrument - VG-ZAB-2F FAB-MS-thioglycerol Molecular mass range ions (m/z): 1249, 1357, 1463; with the addition of NaCl (m/z): 1271, 1379, 1485, 1597. FAB-MS-MB (MB: matrix, m.w. 154); Molecular mass range ions (m/z): 1249, 1283, 1403, 1555; with the addition of NaCl (m/z): 1249, 1271, 1303, 1425, 1483, 1577. FAB-MS-glycerol-DMSO: Molecular mass range ions (m/z): 1215, 1247, 1279, 1293, 1325, |

Figure 10:
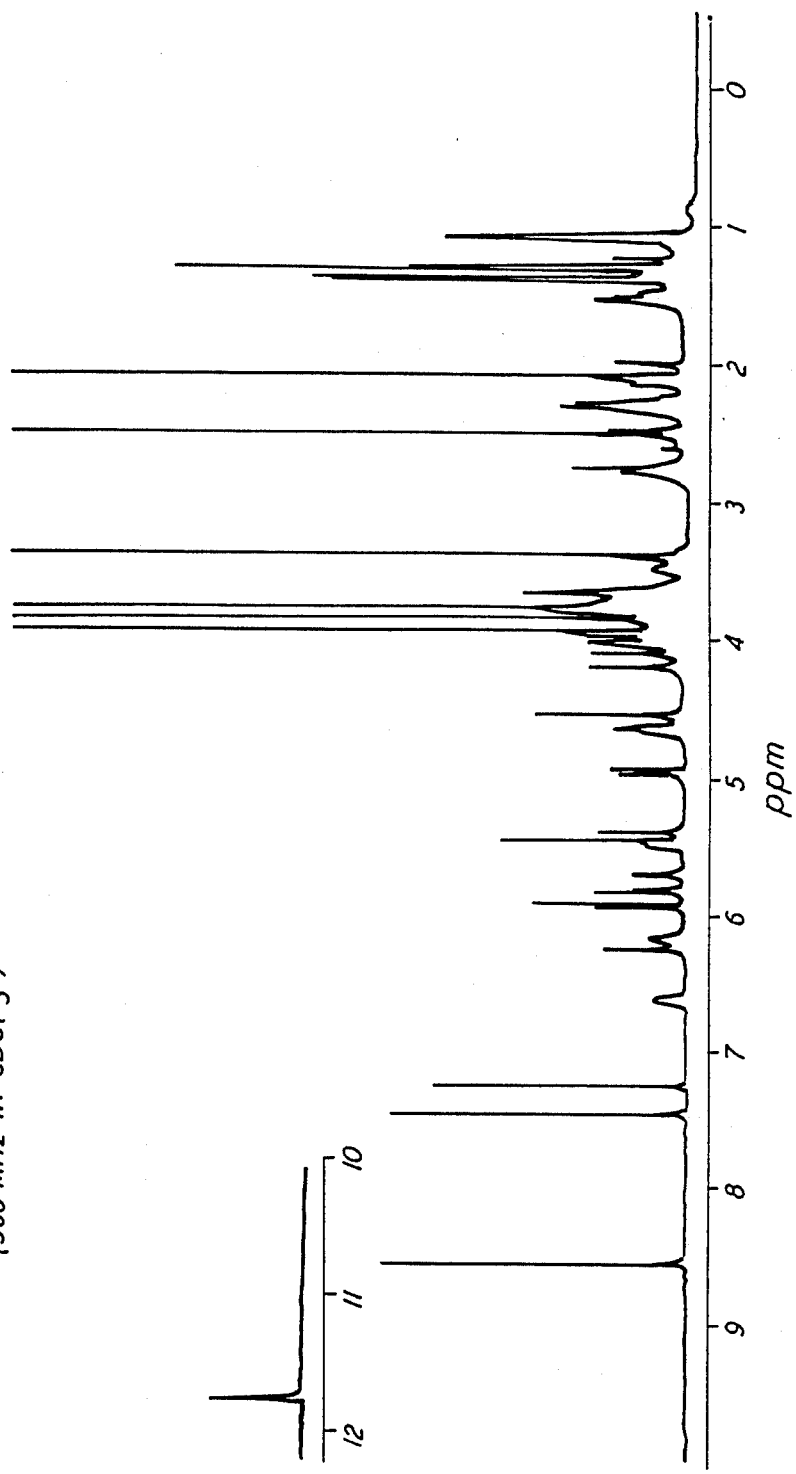
FIG. 10 shows the proton magnetic resonance spectrum of purified BBM-1675 $A_1$ in CDCl$_3$ (360 MHz).
Figure 11:
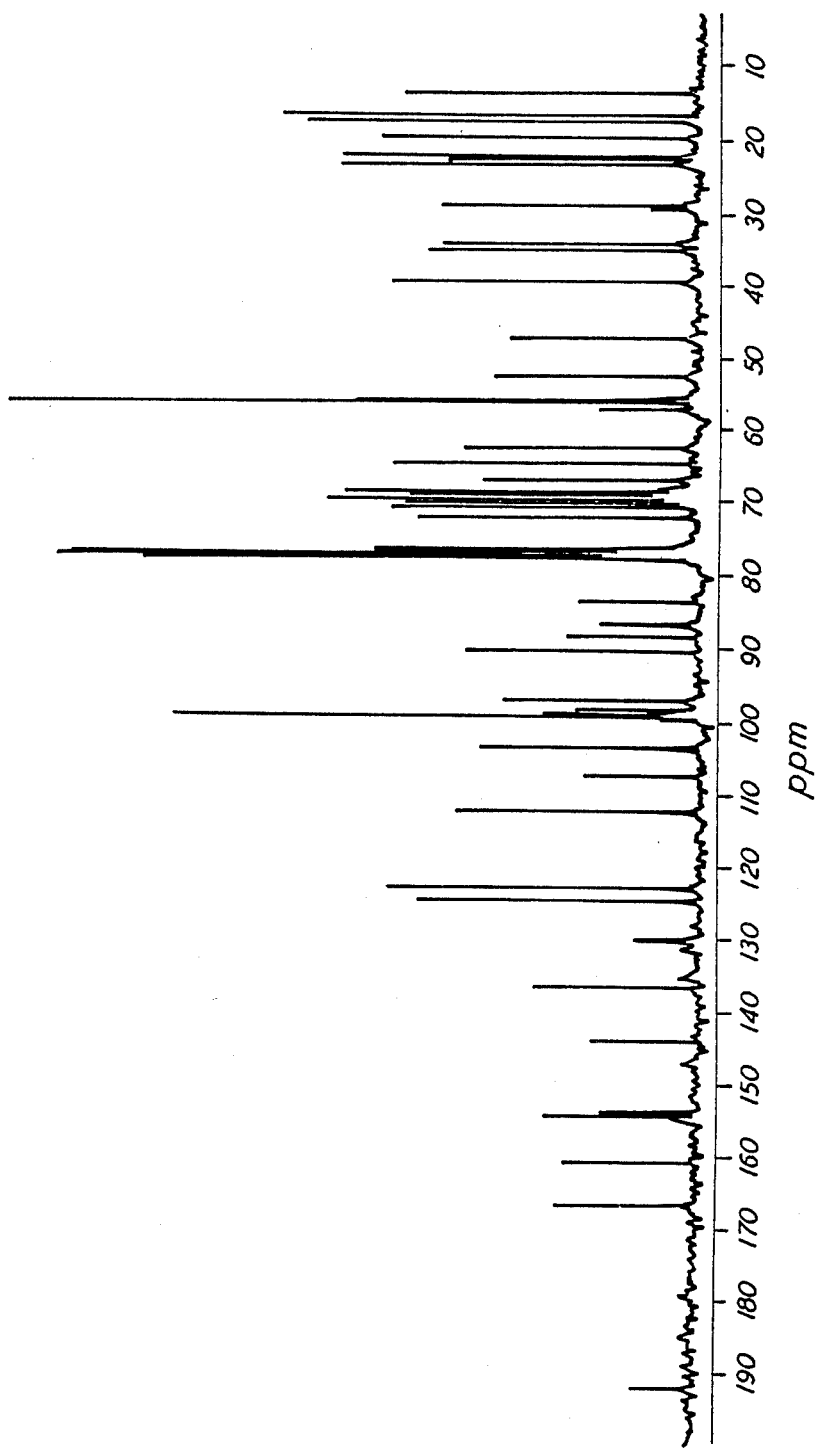
FIG. 11 shows the $^{13}$C magnetic resonance spectrum of purified BBM-1675 $A_1$ in CDCl$_3$ (90.3 MHz).

| | |
|---|---|
| | 1353; with addition of NaCl (m/z): 1215, 1237, 1247, 1269, 1325, 1347, 1375. Instrument: Kratos MS-50 FAB-MS-thioglycerol; Molecular mass range ions (m/z): 1357, 1463. |
| Molecular weight (based on above-described mass spectral data): | apparent MW = 1248 |
| Nuclear Magnetic Resonance Spectra: | Instrument - WM360 Brucker Solvent: $CDCl_3$ $^1$NMR: 360 MHz δ(ppm): 11.75 (1H, s); 8.55 (1H, s); 7.45 (1H, s); 6.61 (1H, m); 6.23 (1H, brs); 6.17 (1H, brs); 5.93 (1H, d, J = 9.3); 5.82 (1H, d, J = 9.3); 5.7 (1H, brs); 5.49 (1H, m); 5.45 (1H, d, J = 2.3); 5.38 (1H, brs); 4.95 (1H, d, J = 10.2); 4.64 (2H, m); 4.54 (1H, d, J = 2.3); 4.2 (1H, s); 4.15–3.35 (26–28H) [4.10 (1H, m); 4.02 (1H, brs); 3.95 (3H, s); 3.85 (3H, s), 3.79 (3H, s); 3.46 (1H, m); 3.40 (3H, s)]; 2.82–2.70 (3H, brm); 2.50 (3H, s), 2.47 (1H, m); 2.38–2.22 (5H); 2.12 (1H, m); 2.11 (3H, s); 1.60–1.05 (22H) [1.39 (3H, d, J = 6.3); 6.31 (3H, d, J = 6.3); 1.29 (3H, d, J = 6.3), 1.08 (6H)] See FIG. 10 $^{13}$C NMR: 90.3 MHz See FIG. 11 |

In a separate test the $^{13}$C NMR spectrum of purified BBM-1675 A$_1$ was determined for a sample dissolved in $CDCl_3$ (80 MHz). Major peaks are indicated below.

| CMR of BBM-1675A$_1$ (80 MHz in CDCL$_3$) Chemical shift in ppm (Multiplicity*) | | | | | |
|---|---|---|---|---|---|
| BBM-1675A$_1$ 13.7(q) | 16.6(q) | 17.5(q) | 19.8(q) | 22.2(q) | 22.6(q) |
| 23.4(q) | 29.0(t) | 34.0(t) | 35.1(t) | 39.5(t) | 47.2(d) |
| 52.5(q) | 55.6(u) | 56.0(d) | 57.1(d) | 62.4(t) | 64.5(d) |
| 67.7(d) | 68.2(d) | 68.8(d) | 69.2(d) | 69.6(d) | 70.2(d) |
| 71.9(d) | 76.0(d) | 76.6(d) | 77.1(u) | 77.3(d) | 83.4(s) |
| 86.6(d) | 88.4(s) | 90.5(t) | 97.2(d) | 98.3(s) | 99.0(d) |
| 99.6(d) | 103.8(d) | 107.6(d) | 112.5(d) | 123.1(d) | 124.9(d) |
| 130.1(d) | 131.5(s) | 134.9(s) | 136.7(s) | 144.0(s) | 147.2(s) |
| 153.8(s) | 154.4(s) | 155.0(s) | 160.7(s) | 166.4(s) | 191.8(s) |

| BBM-1675A$_2$ | |
|---|---|
| Description: | white crystals; mp 147–149° C. |
| Elemental analysis: | C: 52.71% |
| | H: 5.94% |
| | N: 3.94% |
| | S: 9.39% |
| | O(by difference): 28.01% |
| Ultraviolet absorption spectra: | Instrument - Varian UV, Cary 219 |
| Solvent: | methanol |
| Concentration: | 0.02052 g/l |

| $λ_{max}$(nm) | absorptivities |
|---|---|
| 320 | 12.2 |
| 282 | 16.3 |
| 252 | 26.2 |
| 214 | 25.8 |

Figure 12:
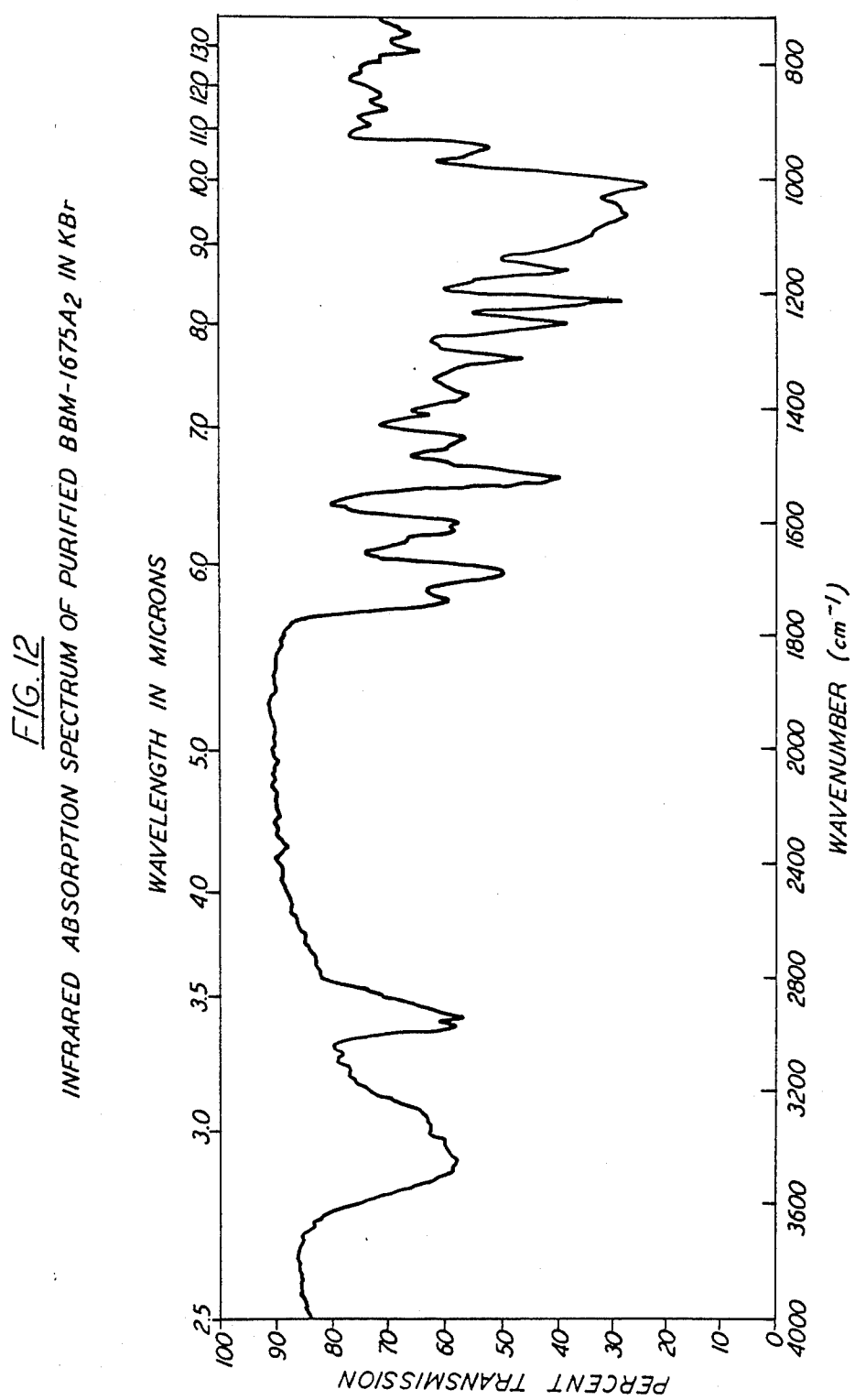
FIG. 12 shows the infrared absorption spectrum of purified BBM-1675 $A_2$ (KBr pellet).

No significant change with acid or base.
Optical rotation: $[α]_D^{27°} = -179.4°$ (c 0.5, CHCl$_3$)
Infrared spectra: See FIG. 12
Instrument: Beckman IR Model 4240
Major absorption bands (KBr): 950, 1015, 1070, 1100, 1155, 1213, 1250, 1313, 1375, 1405, 1450, 1520, 1595, 1610, 1685, 1735, 2940, 2980, 3440, cm$^{-1}$.
Mass Spectra: Instrument: VG-ZAB-2F
FAB-MS-thioglycerol
Molecular mass range ions (m/z): 968, 1249, 1355, 1357, 1463, 1569; with the addition of NaCl (m/z): 990, 1271, 1379, 1485, 1593
FAB-MS-MB (MB: matrix, m.w. 154);
Molecular mass range ions (m/z): 1249, 1403, 1419, 1555, 1571, 1587; with the addition of NaCl

Figure 13:
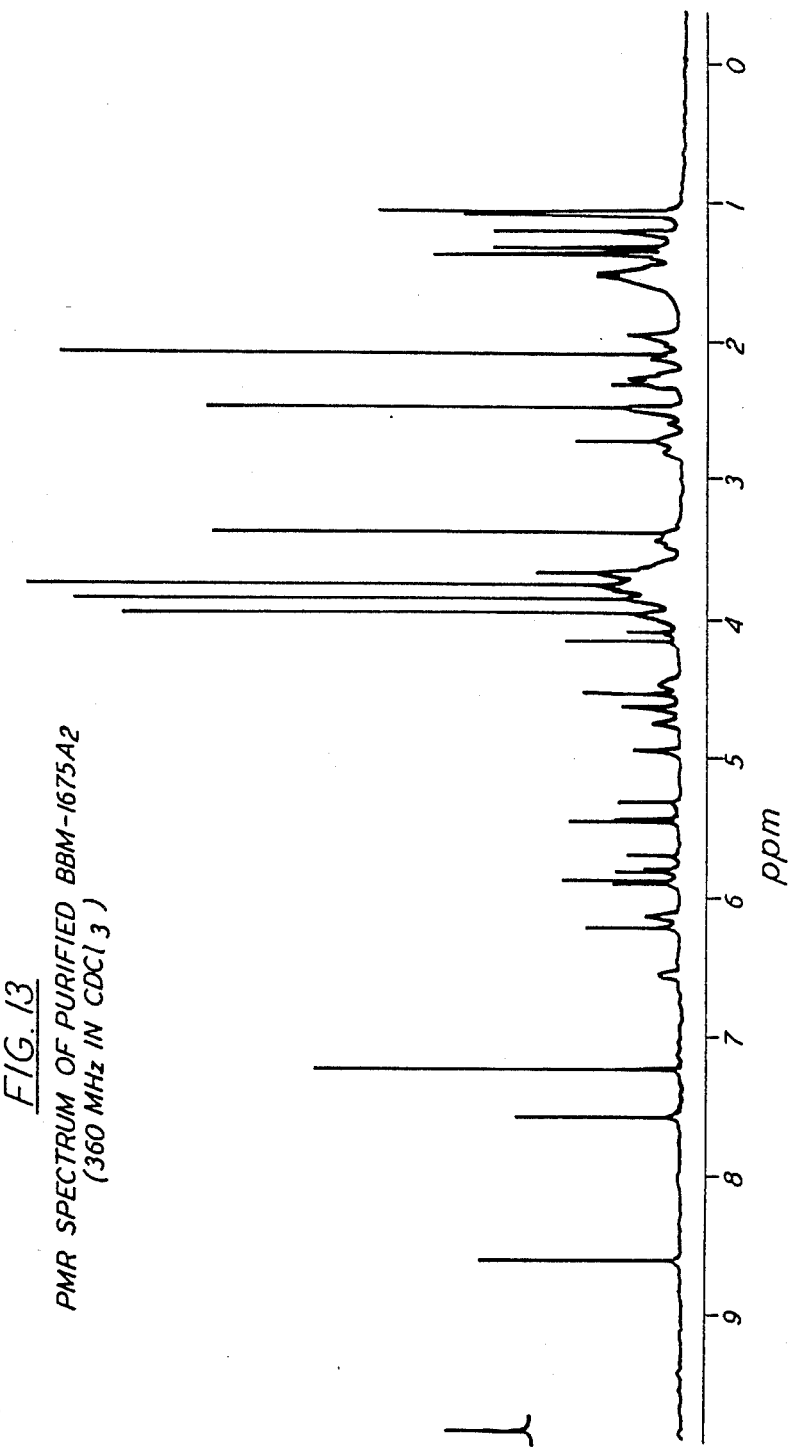
FIG. 13 shows the proton magnetic resonance spectrum of purified BBM-1675 $A_2$ in CDCl$_3$ (360 MHz).

| | |
|---|---|
| | (m/z): 1249, 1271, 1425, 1441, 1457, 1483, 1577. FAB-MS-glycerol-DMSO; Molecular mass range ions (m/z): 1215, 1231, 1247, 1263, 1279, 1293, 1309, 1325, 1326, 1341, 1353, 1369. |
| Molecular weight: (based on above-described mass spectral data) | apparent MW = 1248 |
| Nuclear Magnetic Resonance Spectra | See FIG. 13 |

Figure 14:
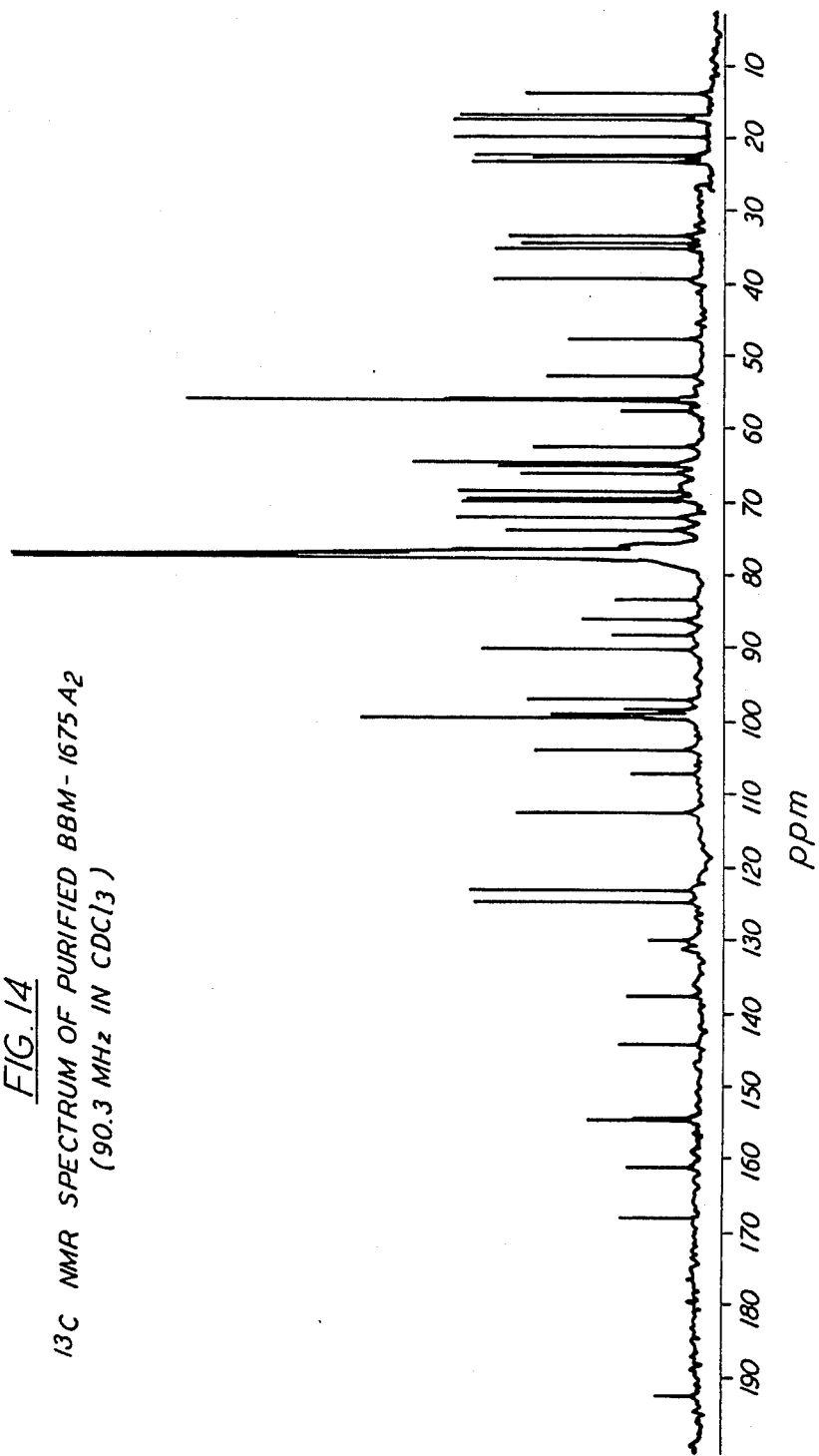
FIG. 14 shows the $^{13}$C magnetic resonance spectrum of purified BBM-1675 $A_2$ in CDCl$_3$ (90.3 MHz).

Instrument: WM 360 Brucker
Solvent: $CDCl_3$
$^1$H NMR 360 MHz δ(ppm): 11.91 (1H, s); 8.62 (1H, s); 7.58 (1H, s); 6.56 (1H, m); 6.22 (1H, s); 6.15 (1H, brs); 5.91 (1H, d, J = 9.6); 5.83 (1H, d, J = 9.6); 5.70 (1H, m); 5.45 (1H, d, J = 2.2); 5.44 (1H, s), 5.34 (1H, brs); 4.95 (1H, d, J = 10.2); 4.75 (1H, m); 4.65 (1H, d, J = 6.8); 4.54 (1H, d, J = 2.2); 4.47 (1H, m); 4.18 (1H, s); 4.10 (1H, brs), 4.05–3.50 (20–24 H); [3.96 (3H, s); 3.87 (3H, s); 3.77 (3H, s)]; 3.46 (1H, m); 3.39 (3H, s); 2.79 (1H, m); 2.73 (2H, m); 2.50 (3H, s); 2.50 (1H, m); 2.38–2.22 (3H); 2.14 (1H, m); 2.10 (3H, s); 1.98 (2H, m); 1.65–1.45 (6–8H); 1.38 (3H, d, J = 6.0); 1.34 (3H, d, J = 6.0); 1.22 (3H, d, J = 6.8); 1.10 (6H).
$^{13}$C NMR 90.3 MHz
See FIG. 14

*Multiplicity - q = quartet; d = doublet; u = uncertain; t = triplet; s = singlet In a separate test the $^{13}$C NMR spectrum of purified BBM-1675A$_2$ was determined for a sample dissolved in CDCl$_3$ (80 MHz). Major peaks are indicated below.

| BBM-1675A$_2$ | | | | | | | |
|---|---|---|---|---|---|---|---|
| 13.7 | 16.9 | 17.5 | 19.8 | 22.3 | 22.7 | 23.4 | 33.1 |
| 34.1 | 35.1 | 39.3 | 47.6 | 52.6 | 55.7 | 56.0 | 56.1 |
| 57.6 | 62.4 | 64.5 | 64.9 | 65.9 | 68.3 | 69.2 | 69.7 |
| 71.9 | 73.6 | 75.8 | 76.1 | 77.1 | 77.7 | 78.1 | 78.3 |
| 83.3 | 86.2 | 88.4 | 90.4 | 97.2 | 98.3 | 99.1 | 99.5 |
| 99.6 | 103.8 | 107.1 | 112.4 | 123.2 | 124.8 | 129.9 | 137.3 |
| 144.1 | 154.2 | 154.5 | 160.9 | 167.9 | 192.2 | | |

TABLE 7
Physico-chemical Properties of BBM-1675 $A_3$, $A_4$, $B_1$, $B_2$

|  |  | $A_3$ | $A_4$ | $B_1$ | $B_2$ |
|---|---|---|---|---|---|
| Melting point (dec): |  | 125–127° C. | 123–126° C. | 159–161° C. | 156–159° C. |
| $[\alpha]_D^{27}$ (c 0.5, $CHCl_3$): |  | −161° C. | −176° C. | −171° C. | −122° C. |
| Anal. Found (%): | C: | 54.55 | 54.65 |  |  |
|  | B: | 6.46 | 6.29 |  |  |
|  | N: | 3.73 | 3.51 |  |  |
|  | S: | 7.49 | 8.07 |  |  |
| UV $\lambda_{max}$ nm ($\Gamma_{1cm}^{1\%}$): |  | 253 (286) | 253 (257) | 253 (225) | 248 (212) |
| in MeOH |  | 282 (158) | 282 (153) | 282 (140) | 279 (141) |
|  |  | 320 (122) | 320 (117) | 320 (104) | 318 (103) |
| in 0.01 N HCl—MeOH: |  | 253 (287) | 253 (258) | 253 (225) | 248 (210) |
|  |  | 282 (160) | 282 (155) | 282 (140) | 279 (140) |
|  |  | 320 (126) | 320 (118) | 320 (105) | 318 (103) |
| in 0.01 N NaOH—MeOH: |  | 252 (280) | 252 (266) | 252 (236) | 248 (233) |
|  |  | 283 (362) | 283 (160) | 283 (141) | 278 (150) |
|  |  | 338 (170) | 319 (118) | 318 (105) | 318 (110) |

Thin-layer Chromatography (TLC) and High Performance Liquid Chromatography (HPLC) Data on BBM-1675 Components A. Study No. 1—Summary

TABLE 8
TLC and HPLC of BBM-1675 components

| | TLC (Rf) | | HPLC (retention time, in minutes) |
|---|---|---|---|
| | $SiO_2$ $CHCl_3$—MeOH (5:1 v/v) | *Silanized $CH_3CN$—$H_2O$ (75:25 v/v) | Lichrosorb RP-18 $CH_3CN$—MeOH—0.1 M $CH_3COONH_4$ (5:2:3 v/v) |
| BBM-1675$A_1$ | 0.74 | 0.18 | 13.3 |
| BM-1675$A_2$ | 0.71 | 0.21 | 17.3 |
| BM-1675$A_3$ | 0.72 | 0.28 | 8.0 |
| M-1675$A_4$ | 0.71 | 0.78 | 5.1 |
| BM-1675$B_1$ | 0.63 | 0.23 | — |
| BBM-1675$B_2$ | 0.60 | 0.16 | — |

*$C_{18}$ reverse phase silica gel

B. Study No. 2—TLC and HPLC for purified $A_1$ and $A_2$ components

TLC Chromatography

Analtech GHLF Silica Gel Uniplates were used for all normal phase chromatography. Plates measuring 2.5 cm × 10 cm were used for one-dimensional TLC. These were developed in glass cylinders measuring 6.4 cm (o.d.) by 12 cm and containing 10 ml of eluant. Plates measuring 7.5 cm × 10 cm were used for two dimensional TLC. The sample was applied to the lower left hand corner 1 cm from the edges. The plate was developed first in a tank (12.7 cm wide, 8.6 cm deep, 13 cm high) containing 50 ml of the first eluant. The plate was then air dried, rotated 90° counterclockwise, and developed in a second tank containing 50 ml of the second eluant.

Whatman analytical precoated C-18 silica gel plates were used for all reverse phase chromatography. Plates measuring 2.5 cm × 7.6 cm were developed in glass cylinders measuring 10 ml of eluant.

Normal phase plates were viewed under 254 nm uv light first. The plates were then inserted into a glass cylinder (6.4 cm o.d. by 12 cm) containing $I_2$ crystals. The plates were then reexamined after approximately 2 minutes. Reversed phase plates were visualized under 254 nm uv light only. Zones were detected by looking for quenching of the fluorescence of an impregnated dye.

Analytical HPLC

The following components were used to construct an analytical HPLC system: Waters Associates Model 6000A Solvent Delivery System pump; Varian Varichrom Model VUV-10 uv/vis Detector set at 254 nm 0.1 OD; Fisher Recordal Series 5000 Recorder; Waters Associates Model 660 Solvent Programmer; Waters Associates Model U6K injector; Alltech, μ-Bondapak $C_{18}$(10μ) column (4.6 mm i.d. × 25 cm) with a Whatman Co. Pell ODS (0.03–0.038 mm) guard column (4.6 mm i.d. × 5 cm). The components were connected with 316 stainless steel tubing (1.6 mm o.d.—0.23 mm i.d.). Eluant was pumped at 2 ml/min for all analysis.

Preparative HPLC

The following components were used to construct a medium pressure liquid chromatography system: Fluid Metering, Inc. Model RP-SY 2CSC FMI Lab Pump; Fluid Metering, Inc. Model PD-60LF FMI Pulse Dampener; a 15 ml sample loop constructed of polypropylene tubing (3.0 mm o.d. × 1.5 mm i.d.) wrapped around a cardboard tube (8.65 cm o.d.); Glenco Series 3500 Universal LC columns; Instrument Specialties Co. Model UA-5 Absorbance/Fluoresence Monitor with a Type 6 optical unit; Instrumentation Specialties Co. Model 590 Flow Interrupter Valve; and an Instrumentation Specialties Co. Model 328 Fraction Collector. The components were connected with polypropylene and Teflon tubing (3.0 mm o.d. × 1.5 mm i.d.) and Glenco multifit connectors and valves in the order listed.

The Glenco series 3500 Universal LC Columns were slurry packed with the defined adsorbent in the designated solvent using standard techniques. The void between the settled bed and tube top was filled with standard Ottawa sand. Eluant was pumped at a maximum rate which would not exceed 60 psi back pressure (approximately 20 ml/min).

Gradient Elution

A Glenco gradient elution apparatus consisting of two chambers of equal diameter, height and volume connected in tandem with a Teflon valve was used for all gradient elutions. One chamber served as a mixing chamber and one as a static reservoir. The less polar solvent was initially held in the mixing chamber. The more polar solvent was held in the static chamber. Teflon coated magnetic stirring bars (1.0×3.7 cm) were placed in both chambers and driven by Thomas Model 15 Magne-matic stirrers. Eluant was pumped from the mixing chamber to the medium pressure HPLC system through polypropylene tubing (1.5 mm ID×3.0 mm OD). As eluant was removed from the mixing chamber, the solvent in the static reservoir was allowed to freely replace it, thus creating a linear gradient of eluant.

TLC ANALYSIS OF BBM-1675A$_1$ and A$_2$

Summarized in Table 9 below are the observed Rf values for BBM-1675A$_1$ and A$_2$ on normal phase plates. Rf is calculated by dividing the measured distance of the center of a zone from the point of sample application by the measured distance of the solvent front from the point of sample application.

TABLE 9

| | Rf | |
|---|---|---|
| System/Compound | BBM-1675A$_1$ | BBM-1675A$_2$ |
| 4% methanol in chloroform | 0.33 | 0.30 |
| 5% methanol in diethyl ether | 0.39 | — |
| 50% acetone in Skellysolve B | 0.38 | 0.31 |

Summarized in Table 10 below are the observed Rf values of BBM-1675A$_1$ and A$_2$ on normal phase plates developed in two dimensions. The position of the spots are expressed in Cartesian coordinates. The X coordinate is the Rf values of the second listed solvent system. The Y coordinate is the Rf values of the first listed solvent system.

TABLE 10

| | Rf | |
|---|---|---|
| System/Compound | BBM-1675A$_1$ | BBM-1675A$_2$ |
| 4% methanol in chloroform vs 5% methanol in diethyl ether | (0.34, 0.33) | (0.28, 0.23) |
| 4% methanol in chloroform vs 50% acetone in Skellysolve B | (0.33, 0.29) | — |

Summarized in Table 11 below are the observed Rf values for BBM-1675A$_1$ and A$_2$ on C-18 reversed phase TLC plates developed in binary eluants.

TABLE 11

| | Rf | |
|---|---|---|
| System/Compound | BBM-1675A$_1$ | BBM-1675A$_2$ |
| 25% 0.5 M NaCl in acetonitrile | 0.18 | 0.21 |
| 25% water in acetonitrile | 0.00 | 0.00 |

Summarized in Table 12 below are the observed Rf values of BBM-1675A$_1$ and A$_2$ on C-18 reversed phase TLC plates developed with ternary eluants.

TABLE 12

| System/Compound | | | Rf | |
|---|---|---|---|---|
| Acetonitrile | Methanol | | BBM-1675A$_1$ | BBM-1675A$_2$ |
| | | 0.5 M NaCl | | |
| 80% | 10% | 10% | 1.00 | 1.00 |
| 60% | 10% | 30% | 0.57 | 0.50 |
| 40% | 30% | 30% | 0.32 | 0.22 |
| 30% | 50% | 20% | 0.44 | 0.33 |
| 50% | 30% | 20% | 0.62 | 0.54 |
| 40% | 40% | 20% | 0.60 | 0.49 |
| 50% | 20% | 20% | 0.42 | 0.34 |
| 60% | 20% | 20% | 0.74 | 0.69 |
| | | water | | |
| 40% | 30% | 30% | 0.00 | 0.00 |
| | | 0.1 M NH$_4$OAc | | |
| 40% | 30% | 30% | 0.32 | 0.22 |
| | | 0.1 M NaH$_2$PO$_4$ | | |
| 40% | 30% | 30% | 0.00 | 0.00 |

HPLC ANALYSIS OF BBM-1675A$_1$ AND A$_2$

BBM-1675A$_1$ and BBM-1675A$_2$ were assayed using single, binary, and ternary eluants on C-18 reversed phase silica gel columns. Summarized in Tables 13, 14 and 15 below are the observed K' values for these compounds. The K' was calculated using the following formula:

$$K' = (T_R - T_0)/T_0$$

where $T_R$ is the retension time measured from time of injection to peak apex and $T_0$ is the void volume time.

TABLE 13

| | K' | |
|---|---|---|
| System/Compound | BBM-1675 A$_1$ | BBM-1675 A$_2$ |
| Acetonitrile | a | a |
| Tetrahydrofuran | a | a |
| Methanol | 0.00 | 0.00 | a = compound did not elute from column.

TABLE 14

| | K' | |
|---|---|---|
| System/Compound | BBM-1675 A$_1$ | BBM-1675 A$_2$ |
| 25% water in acetonitrile | a | a |
| 25% methanol in water | 1.25 | 1.25 | a = compound did not elute from column.

TABLE 15

| Ternary Eluants | | | | |
|---|---|---|---|---|
| System/Compound | | | K' | |
| Acetonitrile | Methanol | | BBM-1675 A$_1$ | BBM-1675 A$_2$ |
| | | water | | |
| 40% | 30% | 30% | a | a |
| | | 0.1 M NH$_4$OAc | | |
| 40% | 30% | 30% | 1.7 | 3.0 |
| 50% | 20% | 30% | 3.8 | 6.5 |
| 43.3% | 23.3% | 33.3% | 6.1 | b |
| 42.5% | 22.5% | 35.0% | 7.8 | b |
| 41.5% | 21.5% | 37.0% | 9.7 | b | a = did not elute
b = not determined

Biological Properties of BBM-1675 Components

Antimicrobial activity of the BBM-1675 components was determined for a veriety of bacteria (gram-positive, gram-negative and acid-fast) and fungi by the serial two-fold agar dilution method. Nutrient agar medium was used for gram-positive and gram-negative bacteria and No. 1001 medium (3% glycerol, 0.3% sodium L-glutamate, 0.2% peptone, 0.31% $Na_2HPO_4$, 0.1% $KH_2PO_4$, 0.005% ammonium citrate, 0.001% $MgSO_4$ and 1.5% agar) for acid-fast organisms. Sabouraud agar medium was used for fungi. As shown in Table 16, each of the six BBM-1675 components ($A_1$, $A_2$, $A_3$, $A_4$, $B_1$, $B_2$) showed a broad spectrum of antimicrobial activity. BBM-1675 $A_1$, $A_2$, $A_3$ and $A_4$ in particular were highly active against gram-positive bacteria.

TABLE 16

Antimicrobial Activity of BBM-1675 Components

| Strain | BBM-1675 $A_1$ | $A_2$ | $A_3$ | $A_4$ | $B_1$ | $B_2$ |
|---|---|---|---|---|---|---|
| S. aureus 209P | <0.0008 | 0.0063 | 0.0063 | 0.0125 | 0.012 | 0.0063 |
| S. aureus Smith | <0.0008 | 0.0031 | 0.0063 | 0.0125 | 0.012 | 0.012 |
| B. subtilis PCI 219 | <0.0008 | 0.05 | 0.0125 | 0.0125 | 0.05 | 0.05 |
| M. luteus 1001 | 0.0016 | 0.0063 | 0.0125 | 0.0125 | 0.1 | 0.1 |
| M. flavus | <0.0008 | 0.0016 | 0.0063 | 0.0125 | 0.025 | 0.025 |
| Mycobacterium 607 | 0.05 | 0.1 | NT | NT | 0.05 | 0.025 |
| E. coli NIHJ | 0.1 | 0.8 | 1.6 | 3.1 | 0.8 | 3.1 |
| K. pneumoniae D11 | 0.4 | 0.8 | 1.6 | 3.1 | 0.8 | 0.8 |
| P. aeruginosa D15 | 0.8 | 1.6 | 1.6 | 3.1 | 3.1 | 3.1 |
| C. albicans IAM 4888 | 0.4 | 0.4 | 1.6 | 6.3 | 3.1 | 1.6 |
| C. neoformans | 1.6 | 3.1 | 1.6 | 6.3 | 6.3 | 12.5 |

MIC in mcg/ml

A second antimicrobial test was carried out on purified $A_1$ and $A_2$ (as prepared in Ex. 3 below) and on components $A_3$ and $A_4$. Data is summarized below.

| Strain | BBM-1675 $A_1$ | $A_2$ | $A_3$ | $A_4$ |
|---|---|---|---|---|
| S. aureus 209P | <0.0008 | 0.0063 | 0.0063 | 0.012 |
| S. aureus Smith | <0.0008 | 0.0031 | 0.0063 | 0.012 |
| B. subtilis PCI 219 | <0.0008 | 0.05 | 0.012 | 0.25 |
| M. luteus 1001 | 0.0016 | 0.0063 | 0.012 | 0.05 |
| M. flavus | <0.0008 | 0.0016 | 0.0063 | 0.012 |
| Mycobacterium 607 | 0.05 | 0.1 | 0.16 | 0.16 |
| E. coli NIHJ | 0.1 | 0.8 | 1.6 | 3.1 |
| K. pneumoniae D11 | 0.4 | 0.8 | 1.6 | 3.1 |
| P. aeruginosa D15 | 0.8 | 1.6 | 3.1 | 3.1 |
| B. fragilis A20928 | 0.2 | 1.6 | 0.2 | 0.4 |
| C. difficile A21675 | 0.4 | 0.8 | 0.05 | 0.4 |
| C. perfringens A9635 | 0.05 | 0.8 | 0.4 | 0.4 |
| C. albicans IAM 4888 | 0.4 | 0.4 | 1.6 | 6.3 |
| C. neoformans | 1.6 | 3.1 | 1.6 | 6.3 |

MIC by ADT (mcg/ml)

The activity of prophage induction in lysogenic bacterium E. coli W1709 (λ) was determined for BBM-1675 components according to the method of Lein et al. in Nature 196: 783–784 (1962). The plaque count was made on agar plates containing test material (T) and control plate (C). A T/C ratio of the plaque counts of greater than 3.0 was considered significant and the lysogenic induction activity (ILB activity) was expressed as the minimum inducible concentration of the test compound. As shown in Table 17, BBM-1675 components showed strong ILB activity in the lysogenic bacteria, thus suggesting that they may possess antitumor activity.

TABLE 17

Lysogenic Induction Activity of BBM-1675 Components

| Antibiotic | MIC* (mcg/ml) |
|---|---|
| BBM-1675 $A_1$ | 0.0063 |
| BBM-1675 $A_2$ | 0.0125 |
| BBM-1675 $A_3$ | 0.05 |
| BBM-1675 $A_4$ | 0.10 |
| BBM-1675 $B_1$ | 0.10 |
| BBM-1675 $B_2$ | 0.20 |

*minimum inducible concentration

The antitumor activity of BBM-1675 $A_1$ and $A_2$ was determined in various mouse tumor systems. Lymphocytic leukemia P-388, lymphoid leukemia L-1210, melanotic melanoma B16 and Lewis lung carcinoma were implanted intraperitoneally into male $BDF_1$ mice at an inoculum size of $10^6$, $10^5$, $5 \times 10^5$ and $10^6$ cells per mouse, respectively. Graded doses of test compounds were administered to the mice intraperitoneally 24 hours after the tumor inoculation. The treatments were given once on the first day only, on day 1, 4 and 7 (q3d×3), once daily for 9 days (qd 1→9) or 11 days (qd 1→11). Components $A_3$ and $A_4$ were tested only against P-388 leukemia by a q3d×3 schedule due to short supply of material.

BBM-1675 $A_1$, $A_2$, $A_3$ and $A_4$ were dissolved in 0.9% saline containing 10% dimethyl sulfoxide, and chromomycin $A_3$ (Toyomycin, Takeda) employed as a reference compound was dissolved in 0.9% saline. Death or survival of the treated and non-treated mice was recorded daily, and the median survival time (MST) was calculated for each of the test (T) and control (C) groups. A T/C value equal to or greater than 125% indicates that a significant antitumor effect was achieved. The results are shown in Tables 18 through 23. BBM-1675 $A_1$ and $A_2$ showed extremely potent antitumor activity against P-388 leukemia with a maximum T/C value of 160%. They are approximately 100 to 3000 times more active than chromomycin $A_3$ in terms of minimum effective dose. BBM-1675 $A_3$ and $A_4$, however, were less active than component $A_1$ or $A_2$ against P-388 leukemia (Table 19). BBM-1675 $A_1$ and $A_2$ were also active against L-1210 leukemia (Table 21), B16 melanoma (Table 22) and Lewis lung carcinoma (Table 23). The toxicity of BBM-1675 $A_1$ and $A_2$ was determined in male ddY mice by intraperitoneal or intravenous administration; BBM-1675 $A_1$ was about 10 times more toxic than BBM-1675 $A_2$ (Table 24). The therapeutic indices of BBM-1675 $A_1$ and $A_2$ were 4 to 8 and 8 to 20 times better than those of chromomycin $A_3$, respectively, in the P-388 leukemia system (Table 25). Second experiments were carried out by intravenous administration of BBM-1675 components against P-388 and L-1210 leukemias, which were inoculated intravenously at $5 \times 10^5$ and $10^4$ cells per mouse, respectively. In these experiments, adriamycin was used as a reference agent, which was dissolved in 0.9% saline and administered on days 1, 4 and 7. The results are shown in Tables 26 and 27. Both components $A_1$ and $A_2$ were superior to adriamycin in terms of maximum T/C value, minimum effective dose and activity range.

TABLE 18

Effect of BBM-1675 Components on P-388 Leukemia (Day 1 treatment)

|  | Dose, ip (mg/kg/day*) | MST (days) | T/C (%) | Average wt. change on day 5 (g) | Survivors on day 5 | Survivors on day 45 |
|---|---|---|---|---|---|---|
| BBM-1675 A₁ | 0.03 | 19.0 | (152) | −2.6 | 5/5 | 0/5 |
|  | 0.01 | 19.0 | (152) | −1.0 | 5/5 | 0/5 |
|  | 0.003 | 18.0 | (144) | −1.0 | 5/5 | 0/5 |
|  | 0.001 | 20.0 | (160) | −1.4 | 5/5 | 0/5 |
|  | 0.0003 | 16.0 | (128) | 0.0 | 5/5 | 0/5 |
|  | 0.0001 | 15.0 | 120 | −0.2 | 5/5 | 0/5 |
|  | 0.00003 | 14.0 | 112 | −0.2 | 5/5 | 0/5 |
| BBM-1675 A₂ | 0.3 | 6.0 | 48 | −3.8 | 3/5 | 0/5 |
|  | 0.1 | 20.0 | (160) | −1.8 | 5/5 | 0/5 |
|  | 0.03 | 18.0 | (144) | −1.4 | 5/5 | 0/5 |
|  | 0.01 | 17.0 | (136) | −0.6 | 5/5 | 0/5 |
|  | 0.003 | 17.0 | (136) | −0.4 | 5/5 | 0/5 |
|  | 0.001 | 16.0 | (128) | 0.0 | 5/5 | 0/5 |
|  | 0.0003 | 15.0 | 120 | 0.0 | 5/5 | 0/5 |
|  | 0.0001 | 14.0 | 112 | 0.0 | 5/5 | 0/5 |
| Chromomycin A₃ | 1 | 19.0 | (152) | −0.2 | 4/5 | 0/5 |
|  | 0.3 | 17.0 | (136) | +0.6 | 5/5 | 0/5 |
|  | 0.1 | 16.0 | (128) | +0.8 | 5/5 | 0/5 |
|  | 0.03 | 14.0 | 112 | 0.0 | 5/5 | 0/5 |
|  | 0.01 | 14.0 | 112 | −0.2 | 5/5 | 0/5 |
| Vehicle | — | 12.5 | — | +0.1 | 10/10 | 0/10 |

*day 1, i.p.
Circle indicates a significant antitumor activity.

TABLE 19

Effect of BBM-1675 Components on P-388 Leukemia (Days 1, 4 and 7 treatment)

|  | Dose, i.p. (mg/kg/day*) | MST (days) | T/C (%) | Average wt. change on day 5 (g) | Survivors on day 5 | Survivors on day 45 |
|---|---|---|---|---|---|---|
| BBM-1675 A₁ | 0.03 | 7.0 | 56 | −2.8 | 5/5 | 0/5 |
|  | 0.01 | 19.0 | (152) | −1.0 | 5/5 | 0/5 |
|  | 0.003 | 19.0 | (152) | −0.6 | 5/5 | 0/5 |
|  | 0.001 | 16.0 | (128) | −0.6 | 5/5 | 0/5 |
|  | 0.0003 | 17.0 | (136) | −0.4 | 5/5 | 0/5 |
|  | 0.0001 | 16.0 | (128) | −0.2 | 5/5 | 0/5 |
|  | 0.00003 | 14.0 | 112 | +0.4 | 5/5 | 0/5 |
| BBM-1675 A₂ | 0.3 | tox. | — | — | 2/5 | 0/5 |
|  | 0.1 | 11.0 | 88 | −1.0 | 5/5 | 0/5 |
|  | 0.03 | 18.0 | (144) | −1.2 | 5/5 | 0/5 |
|  | 0.01 | 18.0 | (144) | −0.4 | 5/5 | 0/5 |
|  | 0.003 | 18.0 | (144) | −0.4 | 5/5 | 0/5 |
|  | 0.001 | 17.0 | (136) | −0.4 | 5/5 | 0/5 |
|  | 0.0003 | 16.0 | (128) | −0.4 | 5/5 | 0/5 |
|  | 0.0001 | 16.0 | (128) | −0.2 | 5/5 | 0/5 |
|  | 0.00003 | 15.0 | 120 | −0.4 | 5/5 | 0/5 |
| BBM-1675 A₃ | 0.01 | 17.5 | (140) | +0.2 | 4/4 | 0/4 |
|  | 0.001 | 15.0 | 120 | +0.6 | 4/4 | 0/4 |
|  | 0.0001 | 13.5 | 108 | +0.6 | 4/4 | 0/4 |
| BBM-1675 A₄ | 0.01 | 16.5 | (132) | +0.2 | 4/4 | 0/4 |
|  | 0.001 | 14.0 | 112 | +0.4 | 4/4 | 0/4 |
|  | 0.0001 | 12.5 | 100 | +0.6 | 4/4 | 0/4 |
| Chromomycin A₃ | 0.3 | 18.0 | (144) | +0.6 | 5/5 | 1/5 |
|  | 0.1 | 18.0 | (144) | +0.6 | 5/5 | 0/5 |
|  | 0.03 | 17.0 | (136) | −0.2 | 5/5 | 0/5 |
|  | 0.01 | 14.0 | 112 | 0.0 | 5/5 | 0/5 |
| Vehicle | — | 12.5 | — | +0.4 | 10/10 | 0/10 |

*days 1, 4 and 7, i.p.
Circle indicates a significant antitumor activity.

TABLE 20

Effect of BBM-1675 Components on P-388 Leukemia (qd 1-9 treatment)

| | Dose, ip (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.01 | 7.0 | 56 | −1.8 | 5/5 | 0/5 |
| | 0.003 | 13.0 | 104 | −1.0 | 5/5 | 0/5 |
| | 0.001 | 19.0 | (152) | −1.2 | 5/5 | 0/5 |
| | 0.0003 | 19.0 | (152) | −0.8 | 5/5 | 0/5 |
| | 0.0001 | 18.0 | (144) | 0.0 | 5/5 | 0/5 |
| | 0.00003 | 16.0 | (128) | +0.2 | 5/5 | 0/5 |
| | 0.00001 | 16.0 | (128) | −0.2 | 5/5 | 0/5 |
| BBM-1675 A$_2$ | 0.1 | 6.0 | 48 | −2.2 | 4/5 | 0/5 |
| | 0.03 | 13.0 | 104 | −1.4 | 5/5 | 0/5 |
| | 0.01 | 18.0 | (144) | −1.0 | 5/5 | 0/5 |
| | 0.003 | 18.0 | (144) | −0.6 | 5/5 | 0/5 |
| | 0.001 | 18.0 | (144) | −0.8 | 5/5 | 0/5 |
| | 0.0003 | 17.0 | (136) | −0.4 | 5/5 | 0/5 |
| | 0.0001 | 16.0 | (128) | −0.4 | 5/5 | 0/5 |
| | 0.00003 | 15.0 | 120 | −0.6 | 5/5 | 0/5 |
| | 0.00001 | 15.0 | 120 | +0.4 | 5/5 | 0/5 |
| Chromomycin A$_3$ | 0.3 | 9.0 | 72 | −2.0 | 5/5 | 0/5 |
| | 0.1 | 18.0 | (144) | +0.4 | 5/5 | 0/5 |
| | 0.03 | 18.0 | (144) | 0.0 | 5/5 | 0/5 |
| | 0.01 | 15.0 | 120 | −0.2 | 5/5 | 0/5 |
| | 0.003 | 13.0 | 104 | −0.2 | 5/5 | 0/5 |
| Vehicle | — | 12.5 | — | +0.4 | 10/10 | 0/10 |

*qd 1 → 9, i.p.
Circle indicates a significant antitumor activity.

TABLE 21

Effect of BBM-1675 Components on L-1210 Leukemia

| | Dose (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.003 | 14.5 | (153) | −1.7 | 6/6 | 0/6 |
| | 0.001 | 12.0 | (126) | −0.5 | 6/6 | 1/6 |
| | 0.0003 | 12.0 | (126) | +0.3 | 6/6 | 0/6 |
| | 0.0001 | 11.0 | 116 | +1.0 | 6/6 | 0/6 |
| BBM-1675 A$_2$ | 0.03 | 10.5 | 111 | −1.5 | 6/6 | 0/6 |
| | 0.01 | 13.5 | (142) | −1.2 | 6/6 | 0/6 |
| | 0.003 | 13.0 | (137) | −0.2 | 6/6 | 0/6 |
| | 0.001 | 11.0 | 116 | +1.3 | 6/6 | 0/6 |
| | 0.0003 | 10.5 | 111 | +1.0 | 6/6 | 0/6 |
| Chromomycin A$_3$ | 0.3 | 8.5 | 89 | −1.2 | 6/6 | 0/6 |
| | 0.1 | 11.5 | 121 | +1.2 | 6/6 | 0/6 |
| | 0.03 | 11.0 | 116 | +1.2 | 6/6 | 0/6 |
| | 0.01 | 11.0 | 116 | +1.3 | 6/6 | 0/6 |
| | 0.003 | 10.0 | 105 | +1.5 | 6/6 | 0/6 |
| Vehicle | — | 9.5 | — | +1.4 | 12/12 | 0/12 |

*qd 1-9, i.p.
Circle indicates a significant antitumor activity.

TABLE 22

Effect of BBM-1675 Components on B16 Melanoma

| | Dose (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.003 | 10.0 | 61 | −0.7 | 6/6 | 0/6 |
| | 0.001 | 31.5 | (191) | 0.0 | 6/6 | 0/6 |
| | 0.0003 | 40.5 | (245) | +0.3 | 6/6 | 0/6 |
| | 0.0001 | 27.0 | (164) | +0.8 | 6/6 | 0/6 |
| | 0.00003 | 22.0 | (133) | +1.8 | 6/6 | 0/6 |
| | 0.00001 | 18.0 | 109 | +2.2 | 6/6 | 0/6 |
| BBM-1675 A$_2$ | 0.03 | 11.0 | 67 | −0.8 | 6/6 | 0/6 |
| | 0.01 | 26.5 | (161) | +0.3 | 6/6 | 0/6 |
| | 0.003 | 29.5 | (179) | +0.2 | 6/6 | 0/6 |
| | 0.001 | 26.0 | (158) | +0.8 | 6/6 | 0/6 |
| | 0.0003 | 22.0 | (133) | +0.2 | 6/6 | 0/6 |
| | 0.0001 | 18.0 | 109 | +0.2 | 6/6 | 0/6 |
| | 0.00003 | 17.0 | 103 | +1.7 | 6/6 | 0/6 |
| Chromomycin A$_3$ | 0.1 | 25.5 | (155) | +2.3 | 6/6 | 0/6 |
| | 0.03 | 23.0 | (139) | +2.2 | 6/6 | 0/6 |
| | 0.01 | 21.0 | (127) | +2.3 | 6/6 | 0/6 |
| | 0.003 | 18.0 | 109 | +2.2 | 6/6 | 0/6 |

TABLE 22-continued

Effect of BBM-1675 Components on B16 Melanoma

|  | Dose (mg/kg/day*) | MST (days) | T/C (%) | Average wt. change on day 5 (g) | Survivors on day 5 | Survivors on day 45 |
|---|---|---|---|---|---|---|
| Vehicle | — | 16.5 | — | +2.1 | 12/12 | 0/12 |

*qd 1-9, i.p.
Circle indicates a significant antitumor activity.

TABLE 23

Effect of BBM-1675 Components on Lewis Lung Carcinoma

|  | Dose (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.003 | 10.0 | 91 | −1.7 | 5/6 | 0/6 |
|  | 0.001 | 31.5 | (286) | −0.7 | 6/6 | 1/6 |
|  | 0.0003 | 21.5 | (195) | −0.7 | 6/6 | 0/6 |
|  | 0.0001 | 21.0 | (191) | +1.0 | 6/6 | 0/6 |
|  | 0.00003 | 13.0 | (118) | +1.0 | 6/6 | 0/6 |
|  | 0.00001 | 11.5 | 105 | +1.0 | 6/6 | 0/6 |
| BBM-1675 A$_2$ | 0.03 | 10.0 | 91 | −1.8 | 6/6 | 0/6 |
|  | 0.01 | 25.5 | (232) | −1.7 | 6/6 | 0/6 |
|  | 0.003 | 28.5 | (259) | 0.0 | 6/6 | 1/6 |
|  | 0.001 | 17.0 | (155) | −0.3 | 6/6 | 0/6 |
|  | 0.0003 | 15.0 | (136) | +1.2 | 6/6 | 0/6 |
|  | 0.0001 | 10.5 | 95 | +0.5 | 6/6 | 0/6 |
|  | 0.00003 | 11.0 | 100 | +0.8 | 6/6 | 0/6 |
| Chromomycin A$_3$ | 0.1 | 21.5 | (195) | +1.2 | 6/6 | 1/6 |
|  | 0.03 | 17.0 | (155) | +1.7 | 5/5 | 0/5 |
|  | 0.01 | 17.0 | (155) | +1.5 | 6/6 | 0/6 |
|  | 0.003 | 11.5 | 105 | +1.7 | 6/6 | 0/6 |
| Vehicle | — | 11.0 | — | +0.8 | 12/12 | 1/12 |

*qd 1-11, i.p.
Circle indicates a significant antitumor activity.

TABLE 24

Toxicity of BBM-1675 Components

|  | LD$_{50}$ (mg/kg/day) Single dose i.p. | LD$_{50}$ (mg/kg/day) Single dose i.v | LD$_{50}$ (mg/kg/day) Multiple dose (gd 1-9) i.p. |
|---|---|---|---|
| BBM-1675 A$_1$ | 0.019 | 0.010 | 0.00046 |
| BBM-1675 A$_2$ | 0.18 | 0.10 | 0.0072 |
| Chromomycin A$_3$ | 0.81 | 0.41 | 0.23 |

TABLE 25

Therapeutic Indices

|  | LD$_{50}$/MED* P-388 Single | LD$_{50}$/MED* P-388 gd 1-9 | L1210 | B16 | LL |
|---|---|---|---|---|---|
| BBM-1675 A$_1$ | 63 | >46 | 2 | 15 | 5 |
| BBM-1675 A$_2$ | 180 | 72 | 2 | 24 | 24 |
| Chromomycin A$_3$ | 8 | 8 | inactive | 23 | 23 |

*minimum effective dose

TABLE 26

Effect of BBM-1675 Components on Intravenously Implanted P-388 Leukemia

|  | Dose (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.01 | 9.5 | 106 | −1.7 | 6/6 | 0/6 |
|  | 0.003 | 14.0 | (156) | −0.3 | 6/6 | 0/6 |
|  | 0.001 | 11.5 | (128) | +0.3 | 6/6 | 0/6 |
|  | 0.0003 | 9.0 | 100 | +0.3 | 6/6 | 0/6 |
| BBM-1675 A$_2$ | 0.1 | 7.0 | 78 | −3.7 | 6/6 | 0/6 |
|  | 0.03 | 15.0 | (167) | −1.0 | 6/6 | 0/6 |
|  | 0.01 | 12.0 | (133) | −0.5 | 6/6 | 0/6 |
|  | 0.003 | 9.0 | 100 | +1.0 | 6/6 | 0/6 |
| Adriamycin | 30 | tox. | — | — | 0/6 | 0/6 |
|  | 10 | 9.0 | 100 | −1.5 | 6/6 | 0/6 |
|  | 3 | 12.0 | (133) | +0.7 | 6/6 | 0/6 |
|  | 1 | 9.0 | 100 | +1.7 | 6/6 | 0/6 |
| Vehicle | — | 9.0 | — | +1.7 | 12/12 | 0/12 |

*days 1, 4 and 7, i.v.
Circle indicates a significant antitumor activity.

TABLE 27

Effect of BBM-1675 Components on Intravenously Implanted L-1210 Leukemia

| | Dose (mg/kg/day*) | MST (days) | T/C (%) | Average wt. change on day 5 (g) | Survivors on day 5 | Survivors on day 45 |
|---|---|---|---|---|---|---|
| BBM-1675 A$_1$ | 0.008 | 9.5 | 119 | −2.0 | 4/6 | 0/6 |
| | 0.004 | 14.0 | (175) | −0.2 | 6/6 | 0/6 |
| | 0.002 | 13.0 | (163) | +0.2 | 6/6 | 0/6 |
| | 0.001 | 9.5 | 119 | +0.8 | 6/6 | 0/6 |
| | 0.0005 | 9.0 | 113 | +0.8 | 6/6 | 0/6 |
| BBM-1675 A$_2$ | 0.063 | 11.0 | (138) | −1.8 | 6/6 | 0/6 |
| | 0.032 | 14.0 | (175) | +0.2 | 6/6 | 0/6 |
| | 0.016 | 10.5 | (131) | +0.8 | 6/6 | 0/6 |
| | 0.008 | 8.0 | 100 | +1.2 | 6/6 | 0/6 |
| | 0.004 | 8.0 | 100 | +0.8 | 6/6 | 0/6 |
| Adriamycin | 16 | tox. | — | — | 2/6 | 0/6 |
| | 8 | 12.0 | (150) | +0.2 | 6/6 | 0/6 |
| | 4 | 9.0 | 113 | +1.5 | 6/6 | 0/6 |
| | 2 | 8.0 | 100 | +1.7 | 6/6 | 0/6 |
| Vehicle | — | 8.0 | — | +1.4 | 12/12 | 0/12 |

*days 1, 4 and 7, i.v.
Circle indicates a significant antitumor activity.

Antitumor activity of components BBM-1675 A$_1$ and A$_2$ was also determined by a second test against P-388 leukemia, L-1210 leukemia and B16 melanoma in mice. Results of these tests are shown below in Tables 28, 29 and 30. Details of the methods used in these tests have been described in Cancer Chemother. Rep. 3: 1–87 (Part 3), 1972.

TABLE 28

Effect of BBM-1675 A$_1$ and A$_2$ on P-388 Leukemia

| Material | Treatment Schedule | Dose, IP ug/kg/day | MST Days | Effect MST % T/C | AWC, gm d.5 | Survivors d.5 (30) |
|---|---|---|---|---|---|---|
| * NSC 38270 | gd1-9 | 400 | 13.0 | 163 | −0.6 | 6/6 |
| | | 200 | 11.0 | 138 | −0.9 | 6/6 |
| BBM-1675 A$_1$ DMSO-saline | d.1 | 51.2 | 20.0 | 250 | −2.1 | 4/6 |
| | | 25.6 | 18.0 | 225 | −1.8 | 6/6 |
| | | 12.8 | 16.5 | 206 | −1.1 | 6/6 |
| | | 6.4 | 13.0 | 163 | +0.1 | 6/6 |
| | | 3.2 | 12.0 | 150 | −0.3 | 6/6 |
| | | 1.6 | 11.0 | 138 | −0.3 | 6/6 |
| | | 0.8 | 10.5 | 131 | 0 | 6/6 |
| | | 0.4 | 10.0 | 125 | +0.4 | 6/6 |
| | | 0.2 | 10.0 | 125 | +0.3 | 6/6 |
| | | 0.1 | 10.0 | 125 | 0 | 6/6 |
| | d.1, 5 & 9 | 25.6 | 8.0 | 100 | −1.8 | 6/6 |
| | | 12.8 | 13.5 | 169 | −1.5 | 6/6 |
| | | 6.4 | 16.5 | 206 | −0.8 | 6/6 |
| | | 3.2 | 16.0 | 200 | −0.8 | 6/6 |
| | | 1.6 | 15.5 | 194 | +0.3 | 6/6 |
| | | 0.8 | 12.5 | 156 | +0.3 | 6/6 |
| | | 0.4 | 12.0 | 150 | −0.1 | 6/6 |
| | | 0.2 | 11.5 | 144 | +0.2 | 6/6 |
| | | 0.1 | 12.0 | 150 | +0.8 | 6/6 |
| | | 0.05 | 10.0 | 125 | +0.8 | 6/6 |
| | gd1-9 | 12.8 | TOX | TOX | TOX | 1/6 |
| | | 6.4 | 6.0 | 75 | −1.5 | 4/6 |
| | | 3.2 | 13.0 | 163 | −1.2 | 6/6 |
| | | 1.6 | 14.5 | 181 | −1.6 | 6/6 |
| | | 0.8 | 16.5 | 206 | −2.3 | 6/6 |
| | | 0.4 | 16.0 | 200 | −0.9 | 6/6 |
| | | 0.2 | 15.0 | 188 | −0.8 | 5/5 |
| | | 0.1 | 13.0 | 163 | −0.4 | 6/6 |
| | | 0.05 | 12.0 | 150 | +0.1 | 6/6 |
| | | 0.025 | 12.0 | 150 | −0.7 | 6/6 |
| BBM-1675 A$_2$ DMSO-saline | d.1 | 256 | TOX | TOX | TOX | 0/6 |
| | | 128 | 12.5 | 156 | −3.5 | 4/6 |
| | | 64 | 27.0 | 338 | −1.9 | 6/6 |
| | | 32 | 26.0 | 325 | −2.0 | 6/6 |
| | | 16 | 16.0 | 200 | −1.8 | 6/6 |
| | | 8 | 15.5 | 194 | −1.9 | 6/6 |
| | | 4 | 15.0 | 188 | −0.7 | 6/6 |
| | | 2 | 12.0 | 150 | −0.5 | 6/6 |
| | | 1 | 12.0 | 150 | 0 | 6/6 |
| | | 0.5 | 10.0 | 125 | +0.2 | 6/6 |
| | d.1, 5 & 9 | 128 | TOX | TOX | TOX | 0/6 |
| | | 64 | TOX | TOX | TOX | 0/6 |
| | | 32 | TOX | TOX | −1.3 | 2/6 |
| | | 16 | 24.5 | 306 | −1.3 | 5/5 |

TABLE 28-continued

Effect of BBM-1675 A₁ and A₂ on P-388 Leukemia

| Material | Treatment Schedule | Dose, IP ug/kg/day | MST Days | Effect MST % T/C | AWC, gm d.5 | Survivors d.5 (30) |
|---|---|---|---|---|---|---|
| | | 8 | 17.5 | 219 | −1.1 | 6/6 |
| | | 4 | 15.0 | 188 | 0 | 6/6 |
| | | 2 | 15.0 | 188 | +0.1 | 6/6 |
| | | 1 | 12.5 | 156 | −0.4 | 6/6 |
| | | 0.5 | 12.0 | 150 | −0.4 | 6/6 |
| BBM-1675 A₂ DMSO-saline | | 0.25 | 11.0 | 138 | −0.4 | 6/6 |
| | gd1-9 | 64 | TOX | TOX | TOX | 1/6 |
| | | 32 | 6.0 | 75 | −2.9 | 4/6 |
| | | 16 | 8.0 | 100 | −1.9 | 6/6 |
| | | 8 | 15.5 | 194 | −1.3 | 6/6 |
| | | 4 | 17.0 | 213 | −1.8 | 6/6 |
| | | 2 | 15.0 | 188 | −1.1 | 6/6 |
| | | 1 | 14.0 | 175 | −0.5 | 6/6 |
| | | 0.5 | 14.0 | 175 | −0.6 | 6/6 |
| | | 0.25 | 12.0 | 150 | −0.1 | 6/6 |
| | | 0.125 | 12.0 | 150 | +0.1 | 6/6 |
| Control | | Saline | 8.0 | — | +0.5 | 10/10 |

Tumor inoculum: 10⁶ ascites cells implanted i.p.
Host: CDF₁ ♀ mice.
Tox: <4/6 mice alive on d.5
Evaluation: MST = median survival time.
Effect: % T/C = (MST treated/MST control) × 100.
Criteria: % T/C ≧ 125 considered significant antitumor activity.
*NSC 36270 = olivomycin A

TABLE 29

Effect of BBM-1675 A₁ and A₂ on L-1210 Leukemia

| Material | Treatment Schedule | Dose, IP ug/kg/inj | MST Days | Effect MST % T/C | AWC, gm d.5 | Survivors on d.5 (30) |
|---|---|---|---|---|---|---|
| BBM-1675 A₁ | d.1 | 51.2 | 12.0 | 171 | −1.1 | 5/6 |
| | | 25.6 | 7.0 | 100 | −2.3 | 6/6 |
| | | 12.8 | 9.0 | 129 | −1.1 | 5/6 |
| | | 6.4 | 9.5 | 136 | −0.5 | 6/6 |
| | | 3.2 | 6.0 | 86 | −1.7 | 6/6 |
| | | 1.6 | 7.0 | 100 | −0.8 | 6/6 |
| | | 0.8 | 8.0 | 114 | −0.4 | 6/6 |
| | | 0.4 | 7.0 | 100 | +0.3 | 6/6 |
| | | 0.2 | 7.0 | 100 | −0.5 | 5/6 |
| | | 0.1 | 7.0 | 100 | +0.8 | 5/6 |
| | d.1, 5 & 9 | 25.6 | TOX | TOX | TOX | 1/6 |
| | | 12.8 | 9.0 | 129 | −1.8 | 6/6 |
| | | 6.4 | 9.0 | 129 | −0.8 | 6/6 |
| | | 3.2 | 8.0 | 114 | −1.9 | 6.6 |
| | | 1.6 | 8.5 | 121 | 0 | 6/6 |
| | | 0.8 | 8.0 | 114 | −0.4 | 6/6 |
| | | 0.4 | 7.5 | 107 | −1.3 | 6/6 |
| | | 0.2 | 8.0 | 114 | 0 | 6/6 |
| | | 0.1 | 8.0 | 114 | +0.4 | 5/6 |
| | | 0.05 | 7.0 | 100 | +0.3 | 6/6 |
| | qd 1-9 | 12.8 | TOX | TOX | −2.4 | 3/6 |
| | | 6.4 | 8.0 | 114 | −1.6 | 6/6 |
| | | 3.2 | 8.0 | 114 | −1.7 | 6/6 |
| | | 1.6 | 9.0 | 129 | −2.1 | 6/6 |
| | | 0.8 | 8.5 | 121 | −1.6 | 6/6 |
| | | 0.4 | 8.0 | 114 | −1.0 | 6/6 |
| | | 0.2 | 8.0 | 114 | −0.5 | 5/6 |
| | | 0.1 | 7.0 | 100 | +0.3 | 6/6 |
| | | 0.05 | 7.0 | 100 | +0.3 | 6/6 |
| | | 0.025 | 6.0 | 86 | −0.6 | 6/6 |
| BBM-1675 A₂ | d.1 | 256 | TOX | TOX | TOX | 0/6 |
| | | 128 | 7.0 | 100 | −1.8 | 5/6 |
| | | 64 | 7.5 | 107 | −1.3 | 4/6 |
| | | 32 | 8.0 | 114 | −2.2 | 5/6 |
| | | 16 | 7.0 | 100 | −2.3 | 6/6 |
| | | 8 | 9.5 | 136 | −1.4 | 6/6 |
| | | 4 | 8.5 | 121 | −1.1 | 6/6 |
| | | 2 | 8.0 | 114 | −0.8 | 6/6 |
| | | 1 | 8.0 | 114 | 0 | 6/6 |
| | | 0.5 | 8.0 | 114 | −0.1 | 6/6 |

TABLE 30
Effect of BBM-1675 A₁ and A₂ on B16 Melanoma

| Material | Dose, IP μg (m) or mg/kg/inj | MST Days | Effect MST % T/C | AWC gm d. 5 | Survivors on d. 10 (61) |
|---|---|---|---|---|---|
| BBM-1675 A₁ | 3.2 M | TOX | TOX | −1.8 | 2/10 |
|  | 1.6 | 16.0 | 64 | −1.8 | 10/10 |
|  | 0.8 | 34.5 | 168 | −1.8 | 10/10 |
|  | 0.4 | 56.5 | 225 | −0.9 | 10/10 (2)b |
|  | 0.2 | 47.0 | 188 | −0.7 | 10/10 |
|  | 0.1 | 37.0 | 148 | −0.4 | 10/10 |
| BBM-1675 A₂ | 16 M | 13.0 | 52 | −2.1 | 10/10 |
|  | 8 | 29.5 | 118 | −2.0 | 10/10 |
|  | 4 | 43.5 | 174 | −1.1 | 10/10 |
|  | 2 | 50.5 | 202 | −2.1 | 10/10 (3)b |
|  | 1 | 0.5 | 140 | −1.0 | 10/10 |
|  | 0.5 | 38.0 | 152 | −1.1 | 10/10 |
| Control | Saline | 25.0 | — | −0.1 | 10/10 |

Tumor inoculum: 0.5 ml of a 10% brei, ip
Host: BDF₁ ♀ mice.
Treatment: qd 1-9
Tox: ≦7/10 mice alive on d. 10
Evaluation: MST = median survival time
Effect: % T/C = (MST treated/MST control) × 100.
Criteria: % T/C ≧ 125 considered significant antitumor activity.

[a]Only one without tumor; MST d.m.o. = 55.0 (220%),
[b]Two without tumor; MST d.m.o. = 46.0 (184%)

After further purification of BBM-1675A₁ according to Example 6, samples of the purified compound were tested against L-1210 leukemia, P-388 leukemia and B16 melanoma in mice. Results of these tests are shown below.

TABLE 31
Effect of Purified BBM-1675A₁ on P388 Leukemia
(Day 1 Treatment)

| Compound | Dose (mg/kg/dose) | Route, schedule | MST Days | T/C (%) | Average wt. change on day 5 | Survivors on day 5 |
|---|---|---|---|---|---|---|
| BBM-1675A₁ | 0.1024 | i.p., qd × 1 | TOX | TOX |  | 0/6 |
|  | 0.0512 |  | 17.5 | 159 | −1.8 | 4/6 |
|  | 0.0256 |  | 16.5 | 150 | −2.6 | 6/6 |
|  | 0.0128 |  | 17.5 | 159 | −1.4 | 6/6 |
|  | 0.0064 |  | 15.5 | 141 | −2.2 | 6/6 |
|  | 0.0032 |  | 15.5 | 141 | −2.5 | 6/6 |
|  | 0.0016 |  | 16.5 | 150 | −1.0 | 6/6 |
|  | 0.0008 |  | 15.0 | 136 | −1.2 | 6/6 |
|  | 0.0004 |  | 15.0 | 136 | −2.0 | 6/6 |
|  | 0.0256 | i.p., q4d × 3; | TOX | TOX | −1.5 | 1/6 |
|  | 0.0128 |  | 10.0 | 91 | −2.5 | 5/6 |
|  | 0.0064 |  | 17.5 | 159 | −1.9 | 6/6 |
|  | 0.0032 |  | 17.0 | 155 | −0.8 | 6/6 |
|  | 0.0016 |  | 17.0 | 155 | −2.0 | 6/6 |
|  | 0.0008 |  | 15.0 | 136 | −1.7 | 6/6 |
|  | 0.0004 |  | 15.0 | 136 | −0.4 | 6/6 |
|  | 0.0002 |  | 13.0 | 118 | −0.8 | 6/6 |
|  | 0.0001 |  | 13.0 | 118 | −1.3 | 6/6 |
|  | 0.00005 |  | 13.5 | 123 | −1.0 | 6/6 |
|  | 0.0128 | i.p., qd × 5; | TOX | TOX |  | 0/6 |
|  | 0.0064 |  | TOX | TOX | −3.6 | 3/6 |
|  | 0.0032 |  | 17.5 | 155 | −2.2 | 5/6 |
|  | 0.0016 |  | 14.5 | 132 | −2.0 | 6/6 |
|  | 0.0008 |  | 15.5 | 141 | −2.2 | 6/6 |
|  | 0.0004 |  | 16.0 | 145 | −2.8 | 6/6 |
|  | 0.0002 |  | 17.0 | 155 | −1.3 | 6/6 |
|  | 0.0001 |  | 14.0 | 127 | −1.6 | 5/6 |
|  | 0.00005 |  | 15.0 | 136 | −1.6 | 6/6 |
|  | 0.000025 |  | 15.0 | 136 | −1.0 | 6/6 |
| Control (vehicle) | 1 × 10⁶ | i.p., q4d × 3; | 11.0 | 100 | −0.7 | 9/9 |

Host: CDFl female mice
Implant level and site: 1 × 10⁶ cells, i.p.

TABLE 32

Effect of Purified BBM-1675A$_1$ on L-1210 Leukemia
(Day 1 Treatment)

| Compound | Dose (mg/kg/dose) | Route, schedule | MST Days | T/C (%) | Average wt. change on day 5 | Survivors on day 5 |
|---|---|---|---|---|---|---|
| BBM-1675A$_1$ | 0.1024 | i.p., qd × 1 | TOX | TOX |  | 1/6 |
|  | 0.0512 |  | TOX | TOX | −2.0 | 0/6 |
|  | 0.0256 |  | 8.0 | 114 | −2.9 | 4/6 |
|  | 0.0128 |  | 11.0 | 157 | −2.0 | 6/6 |
|  | 0.0064 |  | 11.0 | 157 | −1.9 | 6/6 |
|  | 0.0032 |  | 10.0 | 143 | −2.0 | 6/6 |
|  | 0.0016 |  | 10.0 | 143 | −2.6 | 5/6 |
|  | 0.0008 |  | 8.0 | 114 | −0.4 | 6/6 |
|  | 0.0256 | i.p., q4d × 3 | TOX | TOX | −2.3 | 2/6 |
|  | 0.0128 |  | 10.5 | 150 | −1.7 | 6/6 |
|  | 0.0064 |  | 11.0 | 157 | −1.8 | 6/6 |
|  | 0.0032 |  | 11.0 | 157 | −1.4 | 6/6 |
|  | 0.0016 |  | 10.5 | 150 | −1.9 | 6/6 |
|  | 0.0008 |  | 9.0 | 129 | −0.6 | 6/6 |
|  | 0.0004 |  | 8.5 | 121 | −0.7 | 6/6 |
|  | 0.0002 |  | 8.0 | 114 | −0.5 | 6/6 |
|  | 0.0128 | i.p., qd × 5 | TOX | TOX | −2.8 | 2/6 |
|  | 0.0064 |  | 7.0 | 100 | −1.8 | 5/6 |
|  | 0.0032 |  | 11.5 | 164 | −1.0 | 6/6 |
|  | 0.0016 |  | 11.0 | 157 | −1.5 | 6/6 |
|  | 0.0008 |  | 10.0 | 143 | −1.6 | 5/6 |
|  | 0.0004 |  | 8.5 | 121 | −0.4 | 6/6 |
|  | 0.0002 |  | 8.5 | 121 | 0.1 | 6/6 |
|  | 0.0001 |  | 8.5 | 121 | 0.0 | 6/6 |
| Control (vehicle) | 1 × 10$^6$ | i.p., qd × 5 | 7.0 | 100 | 0.1 | 10/10 |

Host: CDF1 female mice
Implant level and site: 1 × 10$^6$ cells, i.p.

TABLE 33

Effect of Purified BBM-1675A$_1$ on B16 Melanoma
(Day 1 Treatment)

| Compound | Dose (mg/kg/dose) | Route, schedule | MST Days | T/C (%) | Average wt. change on day 5 | Survivors on day 5 |
|---|---|---|---|---|---|---|
| *BBM-1675A$_1$ | 0.0064 | i.p., q4d × 3 | 16.5 | 110 | −3.8 | 8/10 |
|  | 0.0032 |  | 22.5 | 150 | −3.0 | 10/10 |
|  | 0.0016 |  | 25.0 | 167 | −1.8 | 10/10 |
|  | 0.0008 |  | 22.0 | 147 | −2.3 | 10/10 |
|  | 0.0004 |  | 24.0 | 160 | −1.8 | 9/10 |
|  | 0.0016 | i.p., qd × 9 | 27.0 | 180 | −3.7 | 10/10 |
|  | 0.0008 |  | 27.0 | 180 | −2.9 | 10/10 |
|  | 0.0004 |  | 26.0 | 173 | −2.3 | 10/10 |
|  | 0.0002 |  | 24.5 | 163 | −2.4 | 10/10 |
|  | 0.0001 |  | 25.5 | 170 | −2.3 | 10/10 |
| Control (vehicle) | 0.5 ML | i.p., qd × 9 | 15.0 | 100 | −0.3 | 10/10 |
| **BBM-1675A$_1$ | 0.0064 | i.v., q4d × 3 | 15.0 | 86 | −4.7 | 10/10 |
|  | 0.0032 |  | 32.5 | 186 | −2.1 | 10/10 |
|  | 0.0016 |  | 26.0 | 149 | −1.4 | 10/10 |
|  | 0.0008 |  | 24.0 | 137 | −0.4 | 10/10 |
|  | 0.0004 |  | 24.5 | 140 | −0.0 | 10/10 |
|  | 0.0064 | i.p., q4d × 3 | 18.0 | 103 | −2.7 | 10/10 |
|  | 0.0032 |  | 23.0 | 131 | −1.4 | 10/10 |
|  | 0.0016 |  | 24.0 | 137 | −0.7 | 10/10 |
|  | 0.0008 |  | 25.5 | 146 | −0.8 | 10/10 |
|  | 0.0004 |  | 21.5 | 123 | −1.4 | 10/10 |
| Control (vehicle) | 0.2 ML | i.v., q4d × 3 | 17.5 | 100 | −0.4 | 10/10 |

Host: BDF1 female mice
*Implant level and site: 0.5 ML 10% BREI, i.p.
**Implant level and site: Fragment, s.c.

The above screening data indicates that the purified BBM-1675A$_1$ component has substantially the same antitumor properties as the less purified sample screened previously. The compound has exceptionally high potency since activity has been demonstrated at a dose of 25 nanograms/kg on a daily times 5 schedule against P-388 leukemia in mice. On tests against P-388 and L-1210 leukemias, BBM-1675A$_1$ is effective whether given as a single injection, day 1, every fourth day for 3 injections, or daily times 5. Against B16 melanoma the compound was equally effective given intravenously to animals bearing subcutaneous tumors as when it was given intraperitoneally to animals bearing ip tumor implants. This property of successful pharmacologic delivery of a drug to a tumor at a distant site is unusual among antitumor antibiotics.

As shown above the BBM-1675 components possess potent antimicrobial activity and are thus useful in the therapeutic treatment of mammals and other animals for infectious diseases caused by such microorganisms. Additionally the components may be utilized for other conventional applications of antimicrobial agents such as disinfecting medical and dental equipment.

The induction of prophage in lysogenic bacteria and the activity shown against mouse tumor systems indicate that the BBM-1675 components are also therapeutically useful in inhibiting the growth of mammalian tumors.

The present invention, therefore, provides a method for therapeutically treating an animal host affected by a microbial infection or by a malignant tumor which comprises administering to said host an effective antimicrobial or tumor-inhibiting dose of BBM-1675 $A_1$, $A_2$, $A_3$, $A_4$, $B_1$ or $B_2$, or a pharmaceutical composition thereof.

In another aspect, the present invention provides a pharmaceutical composition which comprises an effective antimicrobial or tumor-inhibiting amount of BBM-1675 $A_1$, $A_2$, $A_3$, $A_4$, $B_1$ or $B_2$ in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BBM-1675 antibiotics used will vary according to the particular component, the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention.

EXAMPLE 1

Fermentation of BBM-1675

Actinomadura strain No. H964-92 was grown and maintained on an agar slant containing 1% malt extract, 0.4% glucose, 0.4% yeast extract, 0.05% $CaCO_3$ and 1.6% agar. A well-grown agar slant was used to inoculate vegetative medium containing 3% soluble starch, 3% dry yeast, 0.3% $K_2HPO_4$, 0.1% $KH_2PO_4$, 0.05% $MgSO_4.7H_2O$, 0.2% NaCl and 0.1% $CaCO_3$, the pH being adjusted to pH 7.0 before sterilization. The vegetative culture was incubated at 32° C. for 72 hours on a rotary shaker (250 rpm) and 5 ml of the growth was transferred into a 500-ml Erlenmeyer flask which contained 100 ml of fermentation medium composed of 3% cane molasses, 1% corn starch, 1% fish meal, 0.1% $CaCO_3$ and 0.005% $CuSO_4.5H_2O$ (pH 7.0 before sterilization). The fermentation was carried out at 28° C. for six days on the rotary shaker. The antibiotic activity in the fermentation broth was determined by the paper-disc agar diffusion using *Staphylococcus aureus* 209P as the test organism. The antibiotic potency reached a maximum of about 1 mcg/ml after five days fermentation.

Fermentation of BBM-1675 was also performed in stir-jar fermenters. Five hundred mililiters of inoculum growth as prepared above was transferred into 20-liter jar fermenters containing 10 liters of fermentation medium which consisted of the same ingredients as used in the shake flask fermentation. The fermentation was carried out at 32° C. with an aeration rate of 12 liters/minute and agitation at 250 rpm. Under these conditions, the antibiotic production reached a maximum of about 0.9 mcg/ml after 68–76 hours of fermentation.

Fermentation studies were also carried out in fermentation tanks. A seed culture was shaken for four days at 30° C. in Erlenmeyer flasks containing vegetative medium consisting of 3% soluble starch, 3% dry yeast, 0.3% $K_2HPO_4$, 0.1% $KH_2PO_4$, 0.05% $MgSO_4.7H_2O$, 0.2% NaCl and 0.1% $CaCO_3$. The seed culture was inoculated to a 200-liter seed tank containing 130 liters of seed medium having the same composition as above, and the seed tank was stirred at 240 rpm at 30° C. for 31 hours. The second seed culture was used to inoculate 3,000 liters of fermentation medium containing 1% corn starch, 3% cane molasses, 1% fish meal, 0.005% $CuSO_4.5H_2O$ and 0.1% $CaCO_3$. The production tank was operated at 28° C. at 164 rpm with an aeration rate of 2,000 liters/minute. The broth pH gradually rose with the progress of fermentation and reached 7.7–7.8 after 170–180 hours, when a peak antibiotic activity of 1.7 mcg/ml was produced.

EXAMPLE 2

Isolation and Purification of BBM-1675 Components

The harvested fermentation broth (3,000 liters, pH 7.8) was separated to mycelial cake and supernate with the aid of a Sharpless centrifuge. The mycelial cake was suspended in 1,600 liters of methanol and the mixture stirred for one hour. The insoluble materials were filtered off and the methanolic extract was concentrated in vacuo to 43 liters. The activity contained in the broth supernate was recovered therefrom by extraction with two 1,000-liter portions of n-butanol. The n-butanol extracts and concentrated methanol extract were combined and evaporated azeotropically by occasional additions of water to an aqueous solution (20 liters) which deposited most of the antibiotic activity as an oily solid. The solid was digested in 30 liters of methanol and the insolubles were removed by filtration. The methanol extract was then concentrated in vacuo to a 10-liter solution, to which was added 40 liters of ethyl acetate and 30 liters of water. After being stirred for 30 minutes, the organic layer was separated, dried over sodium sulfate and evaporated in vacuo to 4 liters. Addition of the concentrate into 20 liters of n-hexane afforded a pale yellow solid of crude BBM-1675 complex (90.14 g, potency: 55 mcg/mg). The complex was shown in TLC to be a mixture of two major components, BBM-1675 $A_1$ and $A_2$, and several minor ones. They were separated and purified by repeated chromatographies which were performed in a cooled room to prevent deterioration.

The BBM-1675 complex (20 g) was dissolved in methanol (20 ml) and charged on a column of Sephadex LH-20 ($\phi 5.5 \times 85$ cm). The column was developed with methanol and the elution monitored by bioassay using *Staphylococcus aureus* 209P. The active eluates were combined, concentrated in vacuo and lyophilized to give a semi-pure solid of BBM-1675 complex (4.19 g). The solid was then chromatographed on a column of silica gel ($\phi 5.0 \times 50$ cm) using chloroform plus an increasing amount (1→5% v/v) of methanol as eluants.

Eluates were pooled on the basis of antibacterial activity (vs. *S. aureus*) and TLC (SiO$_2$; CHCl$_3$—CH$_3$OH=5:1 v/v) and concentrated in vacuo. Nearly homogeneous BBM-1675 A$_1$ (yield after evaporation: 351 mg) was eluted first with 2% methanol in chloroform and then a mixture of BBM-1675 A$_2$, A$_3$ and A$_4$ (507 mg) followed by BBM-1675 B mixture (210 mg) with 3% methanol in chloroform. The solid of BBM-1675 A$_1$ was applied on a column of Sephadex LH-20 ($\phi 2.0 \times 80$ cm) which was developed with methanol. The active fractions were concentrated in vacuo to dryness and the residual solid was crystallized from methanol to afford colorless plates of pure BBM-1675 A$_1$ (124 mg) (this material is starting material for Example 3A.). The complex BBM-1675 A$_2$, A$_3$ and A$_4$ was separated by chromatography on a column of Bondapak C$_{18}$ (Waters, $\phi 3.0 \times 50$ cm). Elution was carried out with aqueous acetonitrile and the bioactive eluates were examined by TLC (Merck, *Silanized: CH$_3$CN—H$_2$O=75:25 v/v). The minor components A$_4$ (33 mg) and A$_3$ (18 mg) were eluted successively in that order with 20% acetonitrile followed by another major component A$_2$ (301 mg) (this material is starting material for Example 3B) with 50% acetonitrile.

*C$_{18}$ reverse phase silica gel

The solid containing BBM-1675 B$_1$ and B$_2$ was chromatographed on a column of silica gel ($\phi 3.0 \times 40$ cm) with chloroform and methanol as the developing solvent. The active fractions eluted with 4% methanol in chloroform were combined and evaporated to afford pure BBM-1675 B$_1$ (7 mg). Another active fraction was eluted at 5% methanol concentration, which upon evaporation afforded BBM-1675 B$_2$ (8 mg).

EXAMPLE 3

Further Purification of BBM-1675 A$_1$ and A$_2$

A. Purification of BBM-1675A$_1$

A 2.67 cm i.d.×75 cm Glenco column was slurry packed with Baker bonded phase octadecyl (C18) silica gel (40 micron particle size) in methanol. The column was connected into a medium pressure HPLC system and equilibrated with 1.5 l of eluant (41.6% acetonitrile—21.6% methanol—36.8% 0.1M ammonium acetate). Partially purified BBM-1675A$_1$ (100.5 mg) obtained according to the purification procedure of Example 2 was dissolved in 2 ml of acetonitrile and drawn into the sample loop. The sample was pumped onto the column. The column was eluted with the above eluant collecting 87 ml fractions. The eluant was monitored at 254 nm and 340 nm. Fractions 55 through 71 were pooled and extracted twice with 1500 ml aliquots of chloroform. The chloroform was evaporated to dryness to yield 89.8 mg of residue C.

A 1.5 cm i.d.×20 cm Glenco column was slurry packed with 12 g of Woelm silica gel (60–200 micron particles). Residue C was applied to the column in a chloroform solution. The column was eluted with a 500 ml linear gradient of chloroform to 10% methanol in chloroform collecting 20–25 ml fractions. After analysis by TLC on silica gel, fractions 6–9 were pooled and evaporated to dryness to yield 73 mg of residue D.

A 1.5 cm i.d.×20 cm Glenco column was slurry packed with 12 g Woelm silica gel (63–200 micron particles) in Skellysolve B. Residue D was dissolved in approximately 2 ml of CHCl$_3$ and applied to the column. The chloroform was displaced with 25 ml of Skellysolve B. The column was then eluted with a 500 ml linear gradient of Skellysolve B to 60% acetone in Skellysolve B collecting 28–25 ml fractions. Fractions 19–23 were pooled and evaporated to dryness to yield 65.6 mg of pure BBM-1675A$_1$.

This residue was homogeneous in three TLC systems (5% methanol in chloroform; 5% methanol in ether; and 50% acetone in Skellysolve B on silica gel) and HPLC (C-18 silica gel —41.5% acetonitrile: 21.5% methanol: 37.0% 0.1M ammonium acetate).

Gel Permeation Chromatography with purified BBM-1675A$_1$

A 2.5 cm i.d.×45 cm Pharmacia column was slurry packed with Sephadex LH-20 in methanol and adjusted to a 33.4 cm chromatography bed. Purified BBM-1675A$_1$ (approximately 120 mg) was dissolved in 2 ml of methanol and transferred to a 2.5 ml sample reservoir. The sample was applied to the column and elution commenced at 1.75 ml/min with methanol collecting 10 ml fractions [Pharmacia Frac-100 fraction collector]. The eluant was monitored at 254 nm with an Isco UA-5 detector. BBM-1675A$_1$ was observed to elute at Ve/Vt of 0.79 to 0.91 (Ve=elution volume; Vt=bed volume).

B. Purification of BBM-1675A$_2$

A 2.65 cm i.d.×75 cm Glenco column was slurry packed with Baker bonded phase octadecyl (C18) silica gel (40 micron particle size) in methanol. The column was connected into the medium pressure HPLC system and equilibrated with 1.5 l of eluant (50% acetonitrile—20% methanol—30% 0.1M ammonium acetate). Partially purified BBM-1675A$_2$ (76.9 mg) as obtained by the procedure of Example 2 was dissolved in 2 ml of acetonitrile and drawn into the sample loop. The sample was pumped onto the column. The column was eluted with the above eluant collecting 87 ml fractions. The eluant was monitored at 254 and 340 nm. Fractions 31 through 38 were pooled and extracted twice with 500 ml aliquots of chloroform. The chloroform was evaporated to dryness to yield 65.8 mg of homogeneous BBM-1675A$_2$.

BBM-1675A$_2$ was homogeneous in 2 TLC systems, one 2-d TLC analysis and HPLC.

EXAMPLE 4

Preferred extraction process for BBM-1675A$_1$

Raw fermentation (6.8 l) obtained according to the general procedure of Example 1 was transferred to a polypropylene bucket (12 cm d, top; 10 cm d, bottom; 37 cm high) equipped with a faucet at the bottom. An equal volume of chloroform was added. The mixture was stirred at a good rate with a CRC-air driven stirrer for 2 hours. Approximately 4 l (1.3 kg) of Dicalite (filter aid) was added and allowed to mix in. The mixture was filtered on a Dicalite pad which was held in a No. 12 Buchner funnel. The filtrate was collected in a 19 l solution bottle equipped with a vacuum take-off (Ace.

No. 5396-06). The mat was washed with 2 liters of chloroform. The filtrate was transferred to a 20 l separatory funnel and the phases allowed to separate. The lower phase (chloroform) was removed.

A 2.5 cm i.d. ×40 cm Glenco tube was slurry packed with 91 g of Woelm silica gel (63-200 micron particles). Using an FMI RPY-2CSD pump, the above chloroform phase was pumped through the column. The column was rinsed with 600 ml of fresh chloroform. The chloroform eluent was discarded. The column was then eluted with 600 ml of 10% methanol in chloroform. This eluant was evaporated to dryness to yield 547 mg of residue A.

Residue A was dissolved into 50 ml of chloroform. The chloroform solution was added to 20 g of Dicalite in a 1 l round bottom flask. A slurry was created by adding approximately 200 ml of Skellysolve B. The solvents were moved in a rotatory evaporator. The residue was slurried in 300 ml of Skellysolve B. The slurry was packed into an Ace flask chromatography tube (Part No. B5872-14) (41 mm id×45.7 cm ) by the following procedure. A glass wool plug was inserted into the throat of the stop cock between the cock and the column tube. A 1 cm layer of standard Ottawa sand was added above the glass wool. The stopcock, glass wool and sand bed were purged of air by passing a pressurized (5.7 psi) flow of Skellysolve B through them. The slurry was then added to the column and allowed to form a packed bed under pressurized flow. The column was never allowed to go dry. After a stable column bed was obtained, a 2 cm layer of Ottawa sand was added onto the top of the bed. The bed was then eluted with an additional 600-700 ml of Skellysolve B. The bed was eluted with 500 ml of toluene. The toluene eluant was evaporated to dryness to yield 93 mg of residue B. This partially purified BBM-1675$A_1$ may then be further purified according to the procedure of Example 3.

EXAMPLE 5

Fermentation of BBM-1675 complex using variant H964-92-A1327Y

A variant strain A1327Y, which was obtained by NTG treatment of *Actinomadura verrucosospora* strain No. H964-92, was used to inoculate vegetative medium containing 2% soluble starch, 1% glucose, 0.5% yeast extract, 0.5% NB-amine type A and 0.1% $CaCO_3$, the pH being adjusted to 7.0 before sterilization. The vegetative culture was incubated at 32° C. for four days on a rotary shaker (250 rpm) and 5 ml of the growth was transferred into a 500 ml Erlenmeyer flask which contained 100 ml of fermentation medium composed of 3% cane molasses, 1% corn starch, 1% fish meal, 0.005% $CuSO_4.5H_2O$, 0.05% $MgSO_4.7H_2O$ and 0.1% $CaCO_3$, the pH being adjusted to 7.0 before sterilization.

The fermentation was carried out at 28° C. for 7 days on the rotary shaker. The antibiotic production reached a maximum of ca. 1.5 mcg/ml.

EXAMPLE 6

Isolation and Purification of BBM-1675 Components

The harvested fermentation broth from Ex. 5 (3,000 L, pH 7.6) was separated to mycelial cake and supernate by using a Sharpless centrifuge. The mycelial cake was stirred with 2,000 L of methanol for one hour and the insoluble materials were removed by filtration. The activity contained in the broth supernate was extracted therefrom with 1,800 L of n-butanol. The methanol and n-butanol extracts were combined and concentrated azeotropically by occasional additions of water to an aqueous solution (20 L) which deposited most of the antibiotic activity as an oily solid. The mixture was shaken three times with 20 L each of ethyl acetate to extract the activity. The extracts were pooled, filtered to remove the insolubles and evaporated in vacuo to 4 L. Addition of the concentrate into 30 L of n-hexane under stirring afforded pale yellow solid of crude BBM-1675 complex (81.7 g, potency: 59 mcg/mg). The complex was shown by TLC and HPLC to be a mixture of two major components, BBM-1675 $A_1$ and $A_2$ and several minor ones. They were separated and purified by a series of chromatographies which were carried out in a cold room to prevent deterioration.

The crude BBM-1675 complex (20 g) was dissolved in methanol (20 ml) and charged on a column of Sephadex LH-20 ($\phi 5.5 \times 85$ cm). The column was developed with methanol and the elution monitored by bioassay using *Staphylococcus aureus* 209P. The active eluates were pooled, concentrated in vacuo and lyophilized to give a semi-pure solid of BBM-1675 complex (4.86 g, potency: 203 mcg/mg). The solid was then chromatographed on a column of silica gel ($\phi 3.0 \times 70$ cm) using chloroform and an increasing amount (1-5%) of methanol as developing solvents. The eluates were pooled on the basis of antibacterial activity against *S. aureus* and TLC ($SiO_2$, $CHCl_3$—MeOH=5:1, v/v) and concentrated in vacuo. BBM-1675 $A_1$ (425 mg after evaporation, potency: 960 mcg/mg) was eluted first with 2% methanol in chloroform and then a mixture of BBM-1675 $A_2$, $A_3$ and $A_4$ (732 mg, potency: 340 mcg/mg) followed by BBM-1675 B complex (200 mg, potency: 190 mcg/mg) with 3% methanol in chloroform. The above BBM-1675 $A_1$ was rechromatographed on silica gel (column: $\phi 2.2 \times 44$ cm) with 2% methanol in benzene. The bioactive eluates were examined by HPLC (Lichrosorb RP-18: $CH_3CN$—MeOH—0.1M$CH_3COONH_4$=5:2:3, v/v) and the fractions containing homogeneous BBM-1675 $A_1$ evaporated in vacuo to dryness. The residual solid was crystallized from methanol (10 ml) to give colorless prisms of BBM-1675 $A_1$ (197 mg, potency: 1,000 mcg/mg).

The complex of BBM-1675 $A_2$, $A_3$ and $A_4$ (537 mg) was separated by column chromatography on Bondapak $C_{18}$ (Waters, $\phi 2.0 \times 42$ cm). Elution was carried out with aqueous acetonitrile and the bioactive eluates were examined by TLC (Merck, silanized: $CH_3CN$—$H_2O$=75.25, v/v). The minor components BBM-1675 $A_4$ (45 mg, potency: 410 mcg/mg) and $A_3$ (19 mg, potency: 300 mcg/mg) were eluted successively with 20% acetonitrile followed by a major component, BBM-1675 $A_2$ (203 mg) with 50% acetonitrile. The BBM-1675 $A_2$ fraction was crystallized from chloroform-n-hexane to deposit colorless rods (70 mg, potency: 290 mcg/mg). The solid containing BBM-1675 B mixture was chromatographed on a column of silica gel ($\phi 3.0 \times 40$ cm) with chloroform and methanol as developing solvent. The active fractions eluted with 4% methanol in chloroform were pooled and evaporated to afford pure BBM-1675 $B_1$ (7 mg, potency: 180 mcg/mg). Another active fraction was eluted at 5% methanol concentration, which upon evaporation afforded BBM-1675 $B_2$ (8 mg, potency: 140 mcg/mg).

We claim:

1. The antitumor antibiotic BBM-1675$B_1$ which:

(a) is soluble in chloroform, ethyl acetate, acetone, ethaol and methanol, slightly soluble in benzene and water, and insoluble in n-hexane and carbon tetrachloride;

(b) give a positive reaction with ferric chloride, Ehrlich and Tollen's reagents and a negative reaction in Sakaguchi, ninhydrin and anthrone tests;

(c) has a melting point in the range of about 159°–161° C.;

(d) has an optical rotation of $[\alpha]_D^{27} -171°$ (c 0.5, $CHCl_3$);

(e) exhibits in silica gel thin layer chromatography an Rf value of 0.63 with the solvent system $CHCl_3$—$CH_3OH$ (5:1 v/v) and exhibits in reverse phase silica gel thin layer chromatography an Rf value of 0.23 with the solvent system $CH_3CN$—$H_2O$ (75:25 v/v);

(f) exhibits the following ultraviolet absorption maxima when dissolved in methanol, 0.01N HCl—$CH_3OH$ and 0.01N NaOH—$CH_3OH$ UV $\lambda_{max}$ nm ($E_{1\ cm}^{1\%}$) in methanol:
253 (225)
282 (140)
320 (104)

UV $\lambda_{max}$ nm ($E_{1\ cm}^{1\%}$) in 0.01N HCl—$CH_3OH$:
253 (225)
282 (140)
320 (105)

UV $\lambda_{max}$ nm ($E_{1\ cm}^{1\%}$) in 0.01N NaOH—$CH_3OH$:
252 (236)
283 (141)
318 (105);

(g) is effective in inhibiting the growth of various bacteria and fungi; and (h) induces prophage in lysogenic bacteria; said antibiotic being obtained by cultivating a BBM-1675$B_1$-producing strain of *Actinomodura verrucosospora* selected from *Actinomadura verrucosospora* strain H964-92 (ATCC 39334), *Actinomadura verrucosospora* strain A1327Y (ATCC 39638), or a BBM-1675$B_1$-producing mutant thereof, in an aqueous nutrient medium containing assimilable sources of carbon and nitrogen under submerged aerobic conditions until a substantial amount of BBM-1675$B_1$ is produced by said organism in said culture medium and then recovering BBM-1675$B_1$ from the culture medium by conventional chromatographic procedures.

2. The antitumor antibiotic BBM-1675 $B_2$ which:

(a) is soluble in chloroform, ethyl acetate, acetone, ethanol and methanol, slightly soluble in benzene and water, and insoluble in n-hexane and carbon tetrachloride;

(b) give a positive reaction with ferric chloride, Ehrlich and Tollen's reagents and a negative reaction in Sakaguchi, ninhydrin and anthrone tests;

(c) has a melting point in the range of about 156°–159° C.;

(d) has an optical rotation of $[\alpha]_D^{27} -122°$ (c 0.5, $CHCl_3$);

(e) exhibits in silica gel thin layer chromatography an Rf value of 0.60 with the solvent system $CHCl_3$—$CH_3OH$ (5:1 v/v) and exhibits in reverse phase silica gel thin layer chromatography an Rf value of 0.16 with the solvent system $CH_3CN$—$H_2O$ (75:25 v/v);

(f) exhibits the following ultraviolet absorption maxima when dissolved in methanol, 0.01N HCl—$CH_3OH$ and 0.01N NaOH—$CH_3OH$ UV $\lambda_{max}$ nm ($E_{1\ cm}^{1\%}$) in methanol:
248 (212)
279 (141)
318 (103)

UV $\lambda_{max}$ nm ($E_{1\ cm}^{1\%}$) in 0.01N HCL—$CH_3OH$:
248 (210)
279 (140)
318 (103)

UV $\lambda_{max}$ nm ($E_{1\ cm}^{1\%}$) in 0.01N NaOH—$CH_3OH$:
248 (233)
278 (150)
318 (110);

(g) is effective in inhibiting the growth of various bacteria and fungi; and (h) induces prophage in lysogenic bacteria; said antibiotic being obtained by cultivating a BBM-1675 $B_2$ producing strain of *Actinomadura verrucosospora* selected from *Actinomadura verrucosospora* strain H964-92 (ATCC 39334), *Actinomadura verrucosospora* strain A1327Y (ATCC 39638), or a BBM-1675$B_2$-producing mutant thereof, in an aqueous nutrient medium containing assimilable sources of carbon and nitrogen under submerged aerobic conditions until a substantial amount of BBM-1675 $B_2$ is produced by said organism in said culture medium and then recovering BBM-1675 $B_2$ from the culture medium by conventional chromatographic procedures.

* * * * *